(12) United States Patent
Byerly et al.

(10) Patent No.: US 11,541,186 B2
(45) Date of Patent: Jan. 3, 2023

(54) DOSE DETECTION AND DRUG IDENTIFICATION FOR A MEDICATION DELIVERY DEVICE

(71) Applicant: Eli Lilly and Company, Indianapolis, IN (US)

(72) Inventors: Roy Howard Byerly, Indianapolis, IN (US); Russell Wayne Perkins, Carmel, IN (US); Rossano Claudio Massari, Lissone (IT); Davide Paccioretti, Samarate (IT)

(73) Assignee: Eli Lilly and Company, Indianapolis, IN (US)

( * ) Notice: Subject to any disclaimer, the term of this patent is extended or adjusted under 35 U.S.C. 154(b) by 548 days.

(21) Appl. No.: 16/488,721

(22) PCT Filed: Feb. 22, 2018

(86) PCT No.: PCT/US2018/019156
§ 371 (c)(1),
(2) Date: Aug. 26, 2019

(87) PCT Pub. No.: WO2018/160425
PCT Pub. Date: Sep. 7, 2018

(65) Prior Publication Data
US 2020/0023137 A1      Jan. 23, 2020

Related U.S. Application Data

(60) Provisional application No. 62/552,556, filed on Aug. 31, 2017, provisional application No. 62/539,106, (Continued)

(51) Int. Cl.
*A61M 5/31* (2006.01)
*A61M 5/315* (2006.01)

(52) U.S. Cl.
CPC .... *A61M 5/31568* (2013.01); *A61M 5/31551* (2013.01); *A61M 2005/3126* (2013.01);
(Continued)

(58) Field of Classification Search
CPC .. A61M 5/31583; A61M 5/3155; A61M 5/20; A61M 5/24; A61M 5/31551;
(Continued)

(56) References Cited

U.S. PATENT DOCUMENTS 5,536,249 A   7/1996  Castellano et al.
5,820,602 A   10/1998 Kovelman et al.
(Continued)

FOREIGN PATENT DOCUMENTS

EP    1074273 B1    9/2004
EP    1353715 B1    5/2005
(Continued)

OTHER PUBLICATIONS

Screen capture from YouTube video clip entitled "*KwikPen: for injecting Humalog, Humalog Mix 25 and Humalog Mix 50*", (at 2:03 of 3:00), 1 page, uploaded on Feb. 13, 2011 by user "manjanest", EndoDiabetes.com video, 2011, Retrieved from Internet: https://www.youtube.com/watch?y=rMCg1Lp2q:w.

Screen capture from YouTube video clip entitled "*Injecting Insulin With the Lantus SoloSTAR Pen*", (at 5:49 of 10:07), 1 page, uploaded on Oct. 29, 2012 by user "胰島素", Sanofi-aventis U.S. LLC, A Sanofi Company video, 2012, Retrieved from Internet: https://www.youtube.com/watch?y=g7JLG36ZO-U.
(Continued)

*Primary Examiner* — Amber R Stiles
(74) *Attorney, Agent, or Firm* — M. Daniel Spillman

(57) ABSTRACT

The present disclosure relates to a dose detection system for use in combination with a medication delivery device. In one aspect, the system includes a module keyed to the device and
(Continued)

including a sensor operable to detect the relative angular position of a sensed element attached to the medication delivery device. The system determines the type of medication contained by the device, and/or the type of device, based on the detected angular position of the sensed element. In another aspect, the dose detection system is used in combination with a medication delivery device including a dose setting member which rotates relative to an actuator during dose delivery. The dose detection system includes a sensor and is operable to detect the relative angular positions of a sensed element attached to the dose setting member during dose delivery and to determine the amount of dose delivered. Related methods are also disclosed.

20 Claims, 21 Drawing Sheets

Related U.S. Application Data filed on Jul. 31, 2017, provisional application No. 62/464,662, filed on Feb. 28, 2017.

(52) U.S. Cl.
CPC ............... *A61M 2205/3306* (2013.01); *A61M 2205/3317* (2013.01)

(58) Field of Classification Search
CPC ...... A61M 2005/2407; A61M 5/31553; A61M 2205/3317; A61M 2205/3515
See application file for complete search history.

(56) References Cited

U.S. PATENT DOCUMENTS

| | | |
|---|---|---|
| 6,248,090 B1 | 6/2001 | Jensen et al. |
| 6,287,283 B1 | 9/2001 | Ljunggreen et al. |
| 6,585,698 B1 | 7/2003 | Packman et al. |
| 6,999,890 B2 | 2/2006 | Kai |
| 7,008,399 B2 | 3/2006 | Larsen et al. |
| 7,291,132 B2 | 11/2007 | DeRuntz et al. |
| 7,511,480 B2 | 3/2009 | Steffen |
| 7,534,230 B2 | 5/2009 | Follman et al. |
| 7,713,229 B2 | 5/2010 | Veit et al. |
| 7,772,835 B2 | 8/2010 | Dmytriw et al. |
| 8,181,849 B2 | 5/2012 | Bazargan et al. |
| 8,385,972 B2 | 2/2013 | Bochenko et al. |
| 8,560,271 B2 | 10/2013 | Koehler et al. |
| 8,638,108 B2 | 1/2014 | Nielsen et al. |
| 8,734,394 B2 | 5/2014 | Adams et al. |
| 8,771,233 B2 | 7/2014 | Watanabe et al. |
| 8,882,704 B2 | 11/2014 | Fago et al. |
| 8,894,611 B2 | 11/2014 | Larsen et al. |
| 9,022,988 B1 | 5/2015 | Shaban |
| 9,089,650 B2 | 7/2015 | Nielsen et al. |
| 9,125,991 B2 | 9/2015 | Schabbach et al. |
| 9,186,465 B2 | 11/2015 | Jorgensen et al. |
| D770,038 S | 10/2016 | Ahlgrim et al. |
| 9,604,004 B2 | 3/2017 | Jakobsen |
| 9,623,188 B2 | 4/2017 | Nielsen et al. |
| 9,775,957 B2 | 10/2017 | Despa et al. |
| 9,782,543 B2 | 10/2017 | Groeschke et al. |
| 9,782,544 B2 | 10/2017 | Heumann et al. |
| 9,943,647 B2 | 4/2018 | Mukai et al. |
| 10,010,678 B2 | 7/2018 | Schildt et al. |
| 10,016,567 B2 | 7/2018 | Denyer et al. |
| 10,155,090 B2 | 12/2018 | Larsen et al. |
| 10,173,020 B2 | 1/2019 | Sutherland et al. |
| 10,383,996 B2 | 8/2019 | Miller et al. |
| 10,391,235 B2 | 8/2019 | Schabbach et al. |
| 10,682,469 B2 | 6/2020 | Jakobsen et al. |
| 2003/0065536 A1 | 4/2003 | Hansen et al. |
| 2005/0038407 A1 | 2/2005 | Sumka |
| 2006/0175427 A1* | 8/2006 | Jonientz ............... G01D 5/2515 239/533.1 |
| 2008/0167615 A1 | 7/2008 | Niehoff |
| 2009/0318865 A1 | 12/2009 | Moller et al. |
| 2012/0072236 A1 | 3/2012 | Atkin |
| 2013/0079727 A1 | 3/2013 | Schildt et al. |
| 2014/0005950 A1 | 1/2014 | Groeschke et al. |
| 2014/0194826 A1 | 7/2014 | Nielsen et al. |
| 2014/0194829 A1 | 7/2014 | Baek et al. |
| 2014/0276583 A1 | 9/2014 | Chen et al. |
| 2015/0025470 A1 | 1/2015 | Baran et al. |
| 2015/0202375 A1 | 7/2015 | Schabbach et al. |
| 2015/0202376 A1 | 7/2015 | Haupt |
| 2015/0246179 A1 | 9/2015 | Zur et al. |
| 2015/0290396 A1 | 10/2015 | Nagar et al. |
| 2015/0352288 A1 | 12/2015 | Andersen |
| 2015/0356273 A1 | 12/2015 | Cave |
| 2016/0030679 A1 | 2/2016 | Neilsen et al. |
| 2016/0051760 A1 | 2/2016 | Krusell et al. |
| 2016/0051764 A1 | 2/2016 | Dreier et al. |
| 2016/0074587 A1 | 3/2016 | Searle et al. |
| 2016/0213853 A1 | 7/2016 | Despa et al. |
| 2016/0235925 A1 | 8/2016 | Kuhn et al. |
| 2016/0239610 A1 | 8/2016 | Andersen |
| 2016/0259913 A1 | 9/2016 | Yu et al. |
| 2016/0263324 A1 | 9/2016 | Shaanan et al. |
| 2016/0287804 A1 | 10/2016 | Madsen et al. |
| 2016/0331906 A1 | 11/2016 | Harms et al. |
| 2016/0378951 A1 | 12/2016 | Gofman et al. |
| 2017/0068799 A1 | 3/2017 | Mensinger et al. |
| 2017/0124284 A1 | 5/2017 | McCullough et al. |
| 2017/0124285 A1 | 5/2017 | McCullough et al. |
| 2017/0232203 A1 | 8/2017 | Krusell |
| 2017/0235920 A1 | 8/2017 | Bauss et al. |
| 2017/0274149 A1 | 9/2017 | Aeschlimann |
| 2017/0286638 A1 | 10/2017 | Searle et al. |
| 2018/0008778 A1 | 1/2018 | Erbstein |
| 2018/0036484 A1 | 2/2018 | Andersen |
| 2018/0099084 A1 | 4/2018 | Schabbach et al. |
| 2018/0154086 A1 | 6/2018 | Toporek et al. |
| 2018/0157803 A1 | 6/2018 | Mirov |
| 2018/0165422 A1 | 6/2018 | Mirov |
| 2018/0225560 A1 | 8/2018 | Schneider et al. |
| 2018/0243511 A1 | 8/2018 | Gylleby et al. |
| 2018/0280624 A1 | 10/2018 | Bitton et al. |
| 2018/0296767 A1 | 10/2018 | Säll |
| 2018/0326164 A1 | 11/2018 | Bauss et al. |
| 2019/0022328 A1 | 1/2019 | Schleicher et al. |
| 2019/0022330 A1 | 1/2019 | Schleicher et al. |

FOREIGN PATENT DOCUMENTS

| | | |
|---|---|---|
| EP | 3042676 | 7/2016 |
| EP | 3103492 | 12/2016 |
| EP | 2945665 B1 | 3/2018 |
| EP | 3517153 | 7/2019 |
| GB | 2256050 A | 11/1992 |
| JP | H08164206 A | 6/1996 |
| JP | 2010525869 A | 7/2010 |
| JP | 2013228313 A | 11/2013 |
| WO | 9009202 | 8/1990 |
| WO | 1999015214 A1 | 4/1999 |
| WO | 02064196 | 8/2002 |
| WO | 2002092153 A2 | 11/2002 |
| WO | 2003047426 A1 | 6/2003 |
| WO | 2004078241 | 9/2004 |
| WO | 2005009231 A1 | 2/2005 |
| WO | 2006069455 A1 | 7/2006 |
| WO | 2007107564 A1 | 9/2007 |
| WO | 2009062675 A1 | 5/2009 |
| WO | 2009132777 | 11/2009 |
| WO | 2010098927 A1 | 9/2010 |
| WO | 2010098928 A1 | 9/2010 |
| WO | 2010098929 A1 | 9/2010 |
| WO | 2010098931 A1 | 9/2010 |
| WO | 2010112575 A1 | 10/2010 |
| WO | 2010142598 A2 | 12/2010 |
| WO | 2012046199 A1 | 4/2012 |
| WO | 2013120778 | 8/2013 |

(56) References Cited

FOREIGN PATENT DOCUMENTS

| | | |
|---|---|---|
| WO | 2014037331 A1 | 3/2014 |
| WO | 2014111340 A1 | 7/2014 |
| WO | 2015189170 A1 | 12/2015 |
| WO | 2016014365 | 1/2016 |
| WO | 2016120207 | 8/2016 |
| WO | 2016131713 | 8/2016 |
| WO | 2016142216 | 9/2016 |
| WO | 2016142727 | 9/2016 |
| WO | 2016155997 | 10/2016 |
| WO | 2016193229 | 12/2016 |
| WO | 2016198516 | 12/2016 |
| WO | 2017013463 | 1/2017 |
| WO | 2017013464 | 1/2017 |
| WO | 2017032586 | 3/2017 |
| WO | 2017050781 | 3/2017 |
| WO | 2017097507 | 6/2017 |
| WO | 2017108312 | 6/2017 |
| WO | 2017148855 | 9/2017 |
| WO | 2017153105 | 9/2017 |
| WO | 2017200989 | 11/2017 |
| WO | 2018013419 | 1/2018 |
| WO | 2018046680 | 3/2018 |
| WO | 2018104289 | 6/2018 |
| WO | 2018104292 | 6/2018 |
| WO | 2018138542 | 8/2018 |
| WO | 2018160425 A1 | 9/2018 |
| WO | 2019001919 A1 | 1/2019 |
| WO | 2019018793 A1 | 1/2019 |
| WO | 2019057911 A1 | 3/2019 |
| WO | 2019057916 A1 | 3/2019 |
| WO | 2019164936 A1 | 8/2019 |

OTHER PUBLICATIONS

Screen capture from YouTube video clip entitled "*How to Use Flexpen for injecting NovoMix 30, Levemir and Novorapid (Novolog) Insulins*", (at 1:25 of 2:22), 1 page, uploaded on Nov. 11, 2012 by user "manjanest", EndoDiabetes Ltd 2009 & 12 video, 2012, Retrieved from Internet: https://www.youtube.com/watch?y=KPlvl0P-yAO.

Screen capture from YouTube video clip entitled "*How to use FlexTouch Insulin Pen for injecting Novorapid (Novolog) and Degludec (Tresiba) Insulins*", (at 1:32 of 2:27), 1 page, uploaded on Nov. 13, 2011 by user "manjanest", EndoDiabetes.com, 2011, Retrieved from Internet: https://www.youtube.com/watch?y=yKTefngYpc.

Screen capture from YouTube video clip entitled "*How to use Humapen Savvio for Injecting Humalog, Humalog Mix 25 and 50 & Humulin I and S*", (at 1:48 of 3:01), 1 page, uploaded on Jun. 12, 2013 by user "manjanest", EndoDiabetes Ltd. video, 2013, Retrieved from Internet: https://www.youtube.com/watch?y=gXKETYM8Fo.

Patent Cooperation Treaty International Search Report pertaining to International Application No. PCT/US2018/019156; International Filing Date: Feb. 22, 2018; dated May 11, 2018.

Patent Cooperation Treaty Written Opinion of the International Searching Authority pertaining to International Application No. PCT/US2018/019156; International Filing Date: Feb. 22, 2018; dated May 11, 2018.

* cited by examiner

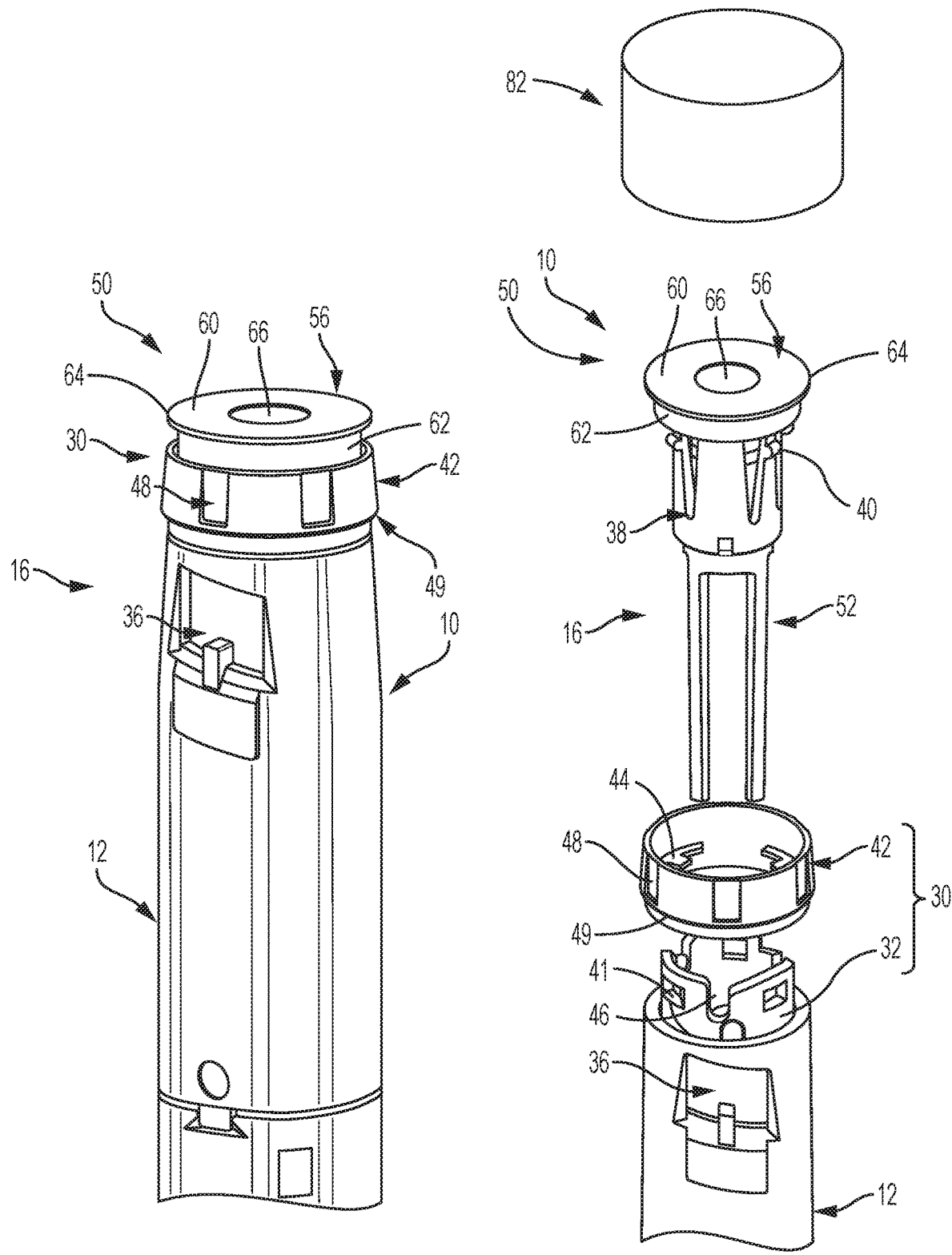

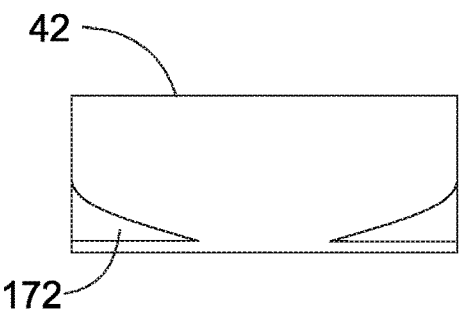
FIG. 13A
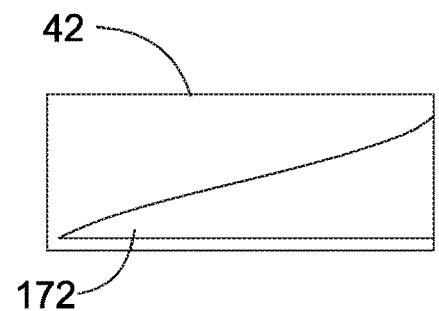
FIG. 13B
FIG. 13C
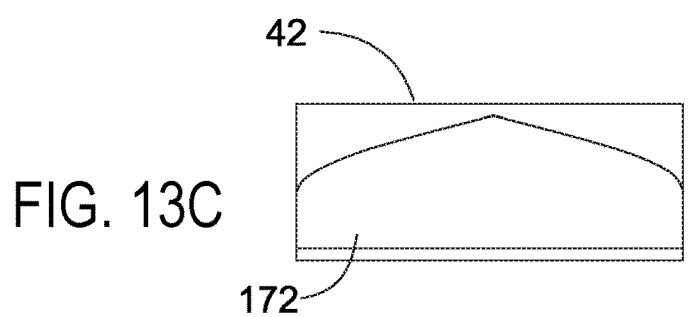
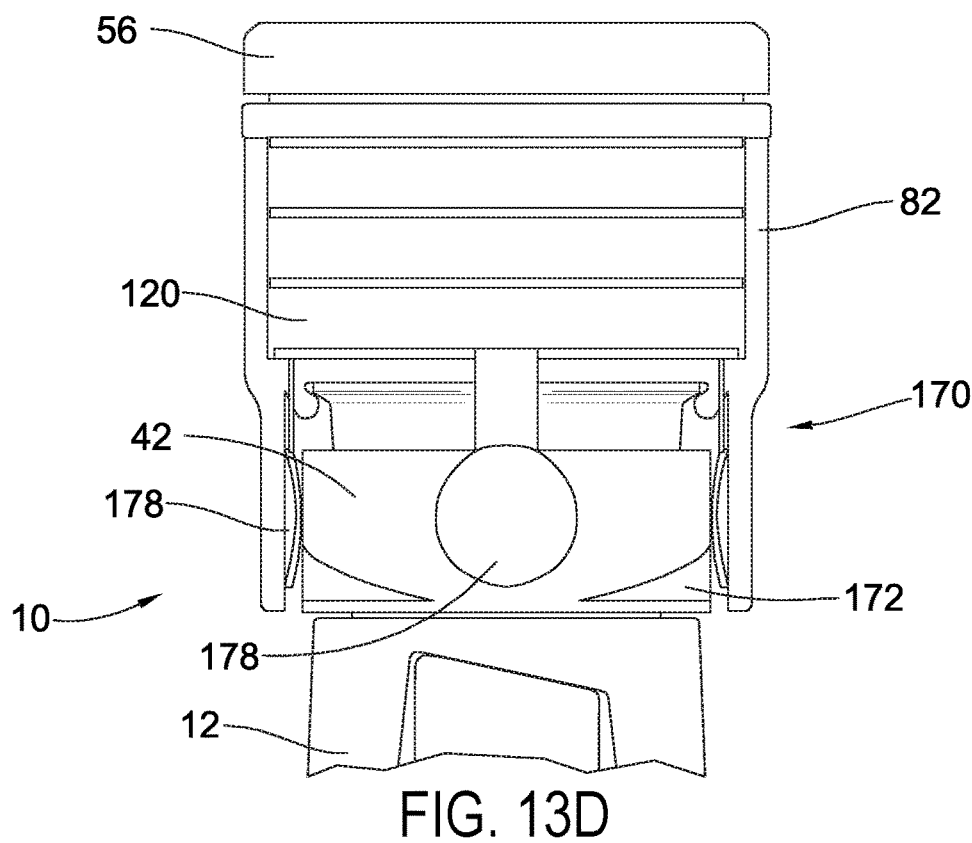
FIG. 13D

DOSE DETECTION AND DRUG IDENTIFICATION FOR A MEDICATION DELIVERY DEVICE

CROSS-REFERENCE TO RELATED APPLICATIONS

The application is a National stage of International Application No. PCT/US2018/019156, filed Feb. 22, 2018, which claims the benefit of U.S. Provisional Application Nos. 62/552,556, filed Aug. 31, 2017, 62/539,106, filed Jul. 31, 2017, and 62/464,662, filed Feb. 28, 2017, each of the applications listed above in its entirety is herein incorporated by reference.

TECHNICAL FIELD

The present disclosure relates to an electronic dose detection system for a medication delivery device, and illustratively to an electronic dose detection module adapted to removably attach to a proximal end portion of a medication delivery device. Alternatively, the dose detection module could be integral to the medication delivery device. The dose delivery detection system is operable to detect the amount of a dose of medication delivered by the medication delivery device and/or the type of drug contained in the medication delivery device.

BACKGROUND

Patients suffering from various diseases must frequently inject themselves with medication. To allow a person to conveniently and accurately self-administer medicine, a variety of devices broadly known as pen injectors or injection pens have been developed. Generally, these pens are equipped with a cartridge including a piston and containing a multi-dose quantity of liquid medication. A drive member is movable forward to advance the piston in the cartridge to dispense the contained medication from an outlet at the distal cartridge end, typically through a needle. In disposable or prefilled pens, after a pen has been utilized to exhaust the supply of medication within the cartridge, a user discards the entire pen and begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

Many pen injectors and other medication delivery devices utilize mechanical systems in which members rotate and/or translate relative to one another in a manner proportional to the dose delivered by operation of the device. Accordingly, the art has endeavored to provide reliable systems that accurately measure the relative movement of members of a medication delivery device in order to assess the dose delivered. Such systems may include a sensor which is secured to a first member of the medication delivery device, and which detects the relative movement of a sensed component secured to a second member of the device.

The administration of a proper amount of medication requires that the dose delivered by the medication delivery device be accurate. Many pen injectors and other medication delivery devices do not include the functionality to automatically detect and record the amount of medication delivered by the device during the injection event. In the absence of an automated system, a patient must manually keep track of the amount and time of each injection. Accordingly, there is a need for a device that is operable to automatically detect the dose delivered by the medication delivery device during an injection event. Further, there is a need for such a dose detection device to be removable and reusable with multiple delivery devices. In other embodiments, there is a need for such a dose detection device to be integral with the delivery device.

It is also important to deliver the correct drug. A patient may need to select either a different drug, or a different form of a given drug, depending on the circumstances. If a mistake is made as to which drug is in the medication delivery device, then the patient will not be properly dosed, and records of dose administration will be inaccurate. The potential for this happening is substantially diminished if a dose detection device is used which automatically confirms the type of drug contained by the medication delivery device.

SUMMARY

The present disclosure relates to a medication delivery device having a dose detection system and an associated control system configured to determine an amount of medication delivered from the medication delivery device based on the sensing of relative rotation within the medication delivery device. The relative rotation may occur between a dose setting member and an actuator and/or housing of the medication delivery device. The dose delivery detection system comprises an electronics assembly attached to the actuator and a sensed component attached to or comprising the dose setting member. The electronics assembly includes a rotation sensor operable with the sensed component to detect the rotation of the dose setting member relative to the actuator during dose delivery. The electronics assembly may further include various additional components such as one or more other sensors, memory, processor, controller, battery, etc. The dose delivery detection system and accompanying electronics assembly may be entirely integral to the pen.

In another aspect, the dose delivery detection system comprises a module which is removably attachable to the medication delivery device. Among other advantages, the attachable and detachable dose delivery detection module is operative to detect a delivered medication amount without changing the functionality or operation of the medication delivery device to which it is attached. In some embodiments, redundant sensors are provided to add robustness to the dose sensing system. In some embodiments, the sensing system records the size of the delivered dose and communicates the information to an external device. Other advantages will be recognized by those of ordinary skill in the art.

In a further aspect, there is provided a dose type detection system which is operable to detect the type of medication delivery device, and/or the type of drug contained in the medication delivery device. The dose type detection system comprises a module which is removably attachable to the actuator member. The module includes a sensor component which is able to detect a sensed component attached to the medication delivery device. The module is keyed to attach to the medication delivery device in a predetermined angular position. The sensor is operable to detect the angular position of the sensed component relative to the sensor to determine the type of drug contained by the medication delivery device.

In another aspect, the module includes both drug delivery and drug type detection systems so as to detect both the amount of drug delivered and the type of drug contained by the medication delivery device. Further included are methods for determining the amount of dose delivered and/or the type of drug contained by the medication delivery device.

BRIEF DESCRIPTION OF THE DRAWINGS

The features and advantages of the present disclosure will become more apparent to those skilled in the art upon consideration of the following detailed description taken in conjunction with the accompanying figures.

FIG. 3 is a perspective view of the proximal portion of the exemplary medication delivery device of FIG. 1.

FIG. 4 is a partially-exploded, perspective view of the proximal portion of the exemplary medication delivery device of FIG. 1, together with a dose delivery detection system of the present disclosure.

FIGS. 12A-D and 13A-G show exemplary embodiments of a dose detection system utilizing inductive sensing.

DETAILED DESCRIPTION

Figure 1:
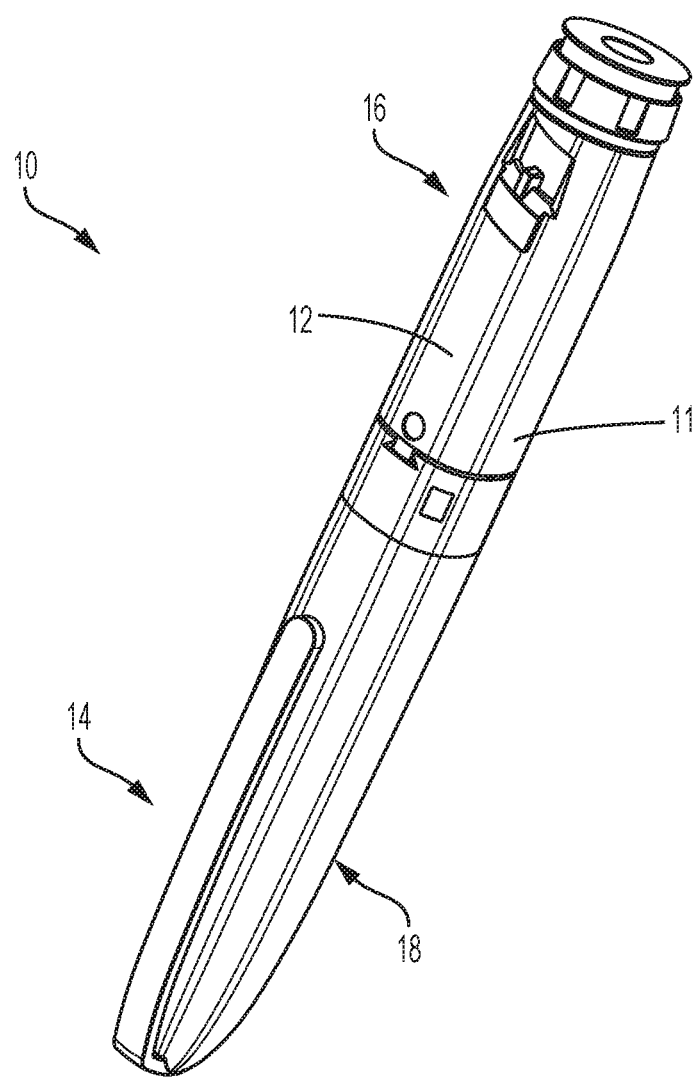
FIG. 1 is a perspective view of an exemplary medication delivery device with which the dose detection system of the present disclosure is operable.

For the purposes of promoting an understanding of the principles of the present disclosure, reference will now be made to the embodiments illustrated in the drawings, and specific language will be used to describe the same. It will nevertheless be understood that no limitation of the scope of the invention is thereby intended.

The present disclosure relates to sensing systems for medication delivery devices. In one aspect, the sensing system is for determining the amount of a dose delivered by a medication delivery device based on the sensing of relative rotational movement between a dose setting member and an actuator of the medication delivery device. The sensed relative angular positions or movements are correlated to the amount of the dose delivered. In a second aspect, the sensing system is for determining the type of drug contained by the medication delivery device. By way of illustration, the medication delivery device is described in the form of a pen injector. However, the medication delivery device may be any device which is used to set and to deliver a dose of a medication, such as an infusion pump, bolus injector or an auto injector device. The medication may be any of a type that may be delivered by such a medication delivery device.

Devices described herein, such as device 10, may further comprise a medication, such as for example, within a reservoir or cartridge 20. In another embodiment, a system may comprise one or more devices including device 10 and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
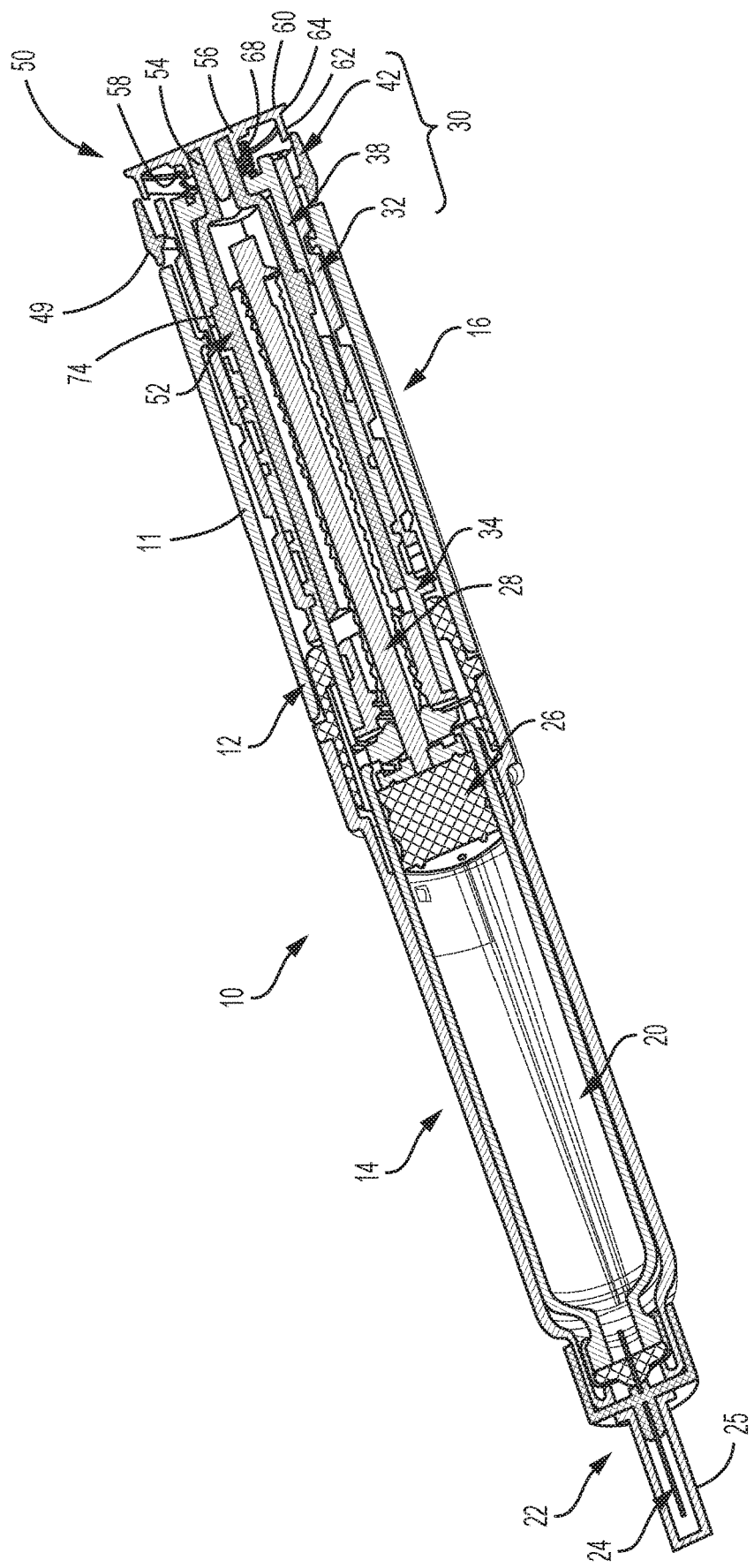
FIG. 2 is a cross-sectional perspective view of the exemplary medication delivery device of FIG. 1.

An exemplary medication delivery device 10 is illustrated in FIGS. 1-4 as a pen injector configured to inject a medication into a patient through a needle. Pen injector 10 includes a body 11 comprising an elongated, pen-shaped housing 12 including a distal portion 14 and a proximal portion 16. Distal portion 14 is received within a pen cap 18. Referring to FIG. 2, distal portion 14 contains a reservoir or cartridge 20 configured to hold the medicinal fluid to be dispensed through its distal outlet end during a dispensing operation. The outlet end of distal portion 14 is equipped with a removable needle assembly 22 including an injection needle 24 enclosed by a removable cover 25. A piston 26 is positioned in reservoir 20. An injecting mechanism positioned in proximal portion 16 is operative to advance piston 26 toward the outlet of reservoir 20 during the dose dispensing operation to force the contained medicine through the needled end. The injecting mechanism includes a drive member 28, illustratively in the form of a screw, axially moveable relative to housing 12 to advance piston 26 through reservoir 20.

A dose setting member 30 is coupled to housing 12 for setting a dose amount to be dispensed by device 10. In the illustrated embodiment, dose setting member 30 is in the form of a screw element operative to spiral (i.e., simultaneously move axially and rotationally) relative to housing 12 during dose setting and dose dispensing. FIGS. 1 and 2 illustrate the dose setting member 30 fully screwed into housing 12 at its home or zero dose position. Dose setting member 30 is operative to screw out in a proximal direction from housing 12 until it reaches a fully extended position corresponding to a maximum dose deliverable by device 10 in a single injection.

Referring to FIGS. 2-4, dose setting member 30 includes a cylindrical dose dial member 32 having a helically threaded outer surface that engages a corresponding threaded inner surface of housing 12 to allow dose setting member 30 to spiral relative to housing 12. Dose dial member 32 further includes a helically threaded inner surface that engages a threaded outer surface of sleeve 34 (FIG. 2) of device 10. The outer surface of dial member 32 includes dose indicator markings, such as numbers that are visible through a dosage window 36 to indicate to the user the set dose amount. Dose setting member 30 further includes a tubular flange 38 that is coupled in the open proximal end of dial member 32 and is axially and rotationally locked to dial member 32 by detents 40 received within openings 41 in dial member 32. Dose setting member 30 further includes a collar or skirt 42 positioned around the outer periphery of dial member 32 at its proximal end. Skirt 42 is axially and rotationally locked to dial member 32 by tabs 44 received in slots 46.

Dose setting member 30 therefore may be considered to comprise any or all of dose dial member 32, flange 38, and skirt 42, as they are all rotationally and axially fixed together. Dose dial member 32 is directly involved in setting the dose and driving delivery of the medication. Flange 38 is attached to dose dial member 32 and, as described later, cooperates with a clutch to selectively couple dial member 32 with a dose button 56. Skirt 42 provides a surface external of body 11 to enable a user to rotate the dial member 32 for setting a dose.

Skirt 42 illustratively includes a plurality of surface features 48 and an annular ridge 49 formed on the outer surface of skirt 42. Surface features 48 are illustratively longitudinally extending ribs and grooves that are circumferentially spaced around the outer surface of skirt 42 and facilitate a user's grasping and rotating the skirt. In an alternative embodiment, skirt 42 is removed or is integral with dial member 32, and a user may grasp and rotate dose button 56 and/or dose dial member 32 for dose setting. A user may grasp and rotate the radial exterior surface of one-piece dose button 56' (shown in FIG. 27), which also includes a plurality of surface features, for dose setting.

Delivery device 10 includes an actuator 50 having a clutch 52 which is received within dial member 32. Clutch 52 includes an axially extending stem 54 at its proximal end. Actuator 50 further includes dose button 56 positioned proximally of skirt 42 of dose setting member 30. In an alternative embodiment, dose setting member 30 comprises one-piece dose button 56', shown in FIG. 27. Dose button 56 includes a mounting collar 58 (FIG. 2) centrally located on the distal surface of dose button 56. Collar 58 is attached to stem 54 of clutch 52, such as with an interference fit or an ultrasonic weld, so as to axially and rotatably fix together dose button 56 and clutch 52.

Dose button 56 includes a disk-shaped proximal end surface or face 60 and an annular wall portion 62 extending distally and spaced radially inwardly of the outer peripheral edge of face 60 to form an annular lip 64 there between. Proximal face 60 of dose button 56 serves as a push surface against which a force can be applied manually, i.e., directly by the user to push actuator 50 in a distal direction. Dose button 56 illustratively includes a recessed portion 66 centrally located on proximal face 60, although proximal face 60 alternatively may be a flat surface. Similarly, one-piece dose button 56' shown in FIG. 27 may include the recessed portion 66 centrally located on proximal face 60 or alternatively may be a flat surface. A bias member 68, illustratively a spring, is disposed between the distal surface 70 of button 56 and a proximal surface 72 of tubular flange 38 to urge actuator 50 and dose setting member 30 axially away from each other. Dose button 56 is depressible by a user to initiate the dose dispensing operation.

Delivery device 10 is operable in both a dose setting mode and a dose dispensing mode. In the dose setting mode of operation, dose setting member 30 is dialed (rotated) relative to housing 12 to set a desired dose to be delivered by device 10. Dialing in the proximal direction serves to increase the set dose, and dialing in the distal direction serves to decrease the set dose. Dose setting member 30 is adjustable in rotational increments (e.g., clicks) corresponding to the minimum incremental increase or decrease of the set dose during the dose setting operation. For example, one increment or "click" may equal one-half or one unit of medication. The set dose amount is visible to the user via the dial indicator markings shown through dosage window 36. Actuator 50, including dose button 56 and clutch 52, move axially and rotationally with dose setting member 30 during the dialing in the dose setting mode.

Dose dial member 32, flange 38 and skirt 42 are all fixed rotationally to one another, and rotate and extend proximally of the medication delivery device 10 during dose setting, due to the threaded connection of dose dial member 32 with housing 12. During this dose setting motion, dose button 56 is rotationally fixed relative to skirt 42 by complementary splines 74 of flange 38 and clutch 52 (FIG. 2), which are urged together by bias member 68. In the course of dose setting, skirt 42 and dose button 56 move relative to housing 12 in a spiral manner from a "start" position to an "end" position. This rotation relative to the housing is in proportion to the amount of dose set by operation of the medication delivery device 10.

Once the desired dose is set, device 10 is manipulated so the injection needle 24 properly penetrates, for example, a user's skin. The dose dispensing mode of operation is initiated in response to an axial distal force applied to the proximal face 60 of dose button 56. The axial force is applied by the user directly to dose button 56. This causes axial movement of actuator 50 in the distal direction relative to housing 12.

The axial shifting motion of actuator 50 compresses biasing member 68 and reduces or closes the gap between dose button 56 and tubular flange 38. This relative axial movement separates the complementary splines 74 on clutch 52 and flange 38, and thereby disengages actuator 50, e.g., dose button 56, from being rotationally fixed to dose setting member 30. In particular, dose setting member 30 is rotationally uncoupled from actuator 50 to allow back-driving rotation of dose setting member 30 relative to actuator 50 and housing 12. The dose dispensing mode of operation may also be initiated by activating a separate switch or trigger mechanism.

As actuator 50 is continued to be axially plunged without rotation relative to housing 12, dial member 32 screws back into housing 12 as it spins relative to dose button 56. The dose markings that indicate the amount still remaining to be injected are visible through window 36. As dose setting member 30 screws down distally, drive member 28 is advanced distally to push piston 26 through reservoir 20 and expel medication through needle 24 (FIG. 2).

During the dose dispensing operation, the amount of medicine expelled from the medication delivery device is proportional to the amount of rotational movement of the dose setting member 30 relative to actuator 50 as the dial member 32 screws back into housing 12. The injection is completed when the internal threading of dial member 32 has reached the distal end of the corresponding outer threading of sleeve 34 (FIG. 2). Device 10 is then once again arranged in a ready state or zero dose position as shown in FIGS. 2 and 3.

The start and end angular positions of dose dial member 32, and therefore of the rotationally fixed flange 38 and skirt 42, relative to dose button 56 provide an "absolute" change in angular positions during dose delivery. Determining whether the relative rotation was in excess of 360° is determined in a number of ways. By way of example, total rotation may be determined by also taking into account the incremental movements of the dose setting member 30 which may be measured in any number of ways by a sensing system.

Further details of the design and operation of an exemplary delivery device 10 may be found in U.S. Pat. No. 7,291,132, entitled Medication Dispensing Apparatus with Triple Screw Threads for Mechanical Advantage, the entire disclosure of which is hereby incorporated by reference herein. Another example of the delivery device is an auto-injector device that may be found in U.S. Pat. No. 8,734,394, entitled "Automatic Injection Device With Delay Mechanism Including Dual Functioning Biasing Member," which is hereby incorporated by reference in its entirety, where such device being modified with one or more various sensor systems described herein to determine an amount of medication delivered from the medication delivery device based on the sensing of relative rotation within the medication delivery device.

The dose detection systems use a sensing component and a sensed component attached to members of the medication delivery device. The term "attached" encompasses any manner of securing the position of a component to another component or to a member of the medication delivery device such that they are operable as described herein. For example, a sensing component may be attached to a member of the medication delivery device by being directly positioned on, received within, integral with, or otherwise connected to, the member. Connections may include, for example, connections formed by frictional engagement, splines, a snap or press fit, sonic welding or adhesive.

The term "directly attached" is used to describe an attachment in which two components, or a component and a member, are physically secured together with no intermediate member, other than attachment components. An attachment component may comprise a fastener, adapter or other part of a fastening system, such as a compressible membrane interposed between the two components to facilitate the attachment. A "direct attachment" is distinguished from a connection where the components/members are coupled by one or more intermediate functional members, such as the way dial member 32 is coupled in FIG. 2 to the dose button 56 by a clutch 52.

The term "fixed" is used to denote that an indicated movement either can or cannot occur. For example, a first member is "fixed rotationally" with a second member if the two members are required to move together in rotation. In one aspect, a member may be "fixed" relative to another member functionally, rather than structurally. For example, a member may be pressed against another member such that the frictional engagement between the two members fixes them together rotationally, while the two members may not be fixed together absent the pressing of the first member.

Various sensor systems are contemplated herein. In general, the sensor systems comprise a sensing component and a sensed component. The term "sensing component" refers to any component which is able to detect the relative position of the sensed component. The sensing component includes a sensing element, or "sensor", along with associated electrical components to operate the sensing element. The "sensed component" is any component for which the sensing component is able to detect the position and/or movement of the sensed component relative to the sensing component. For the dose delivery detection system, the sensed component rotates relative to the sensing component, which is able to detect the angular position and/or the rotational movement of the sensed component. For the dose type detection system, the sensing component detects the relative angular position of the sensed component. The sensing component may comprise one or more sensing elements, and the sensed component may comprise one or more sensed elements. The sensor system is able to detect the position or movement of the sensed component(s) and to provide outputs representative of the position(s) or movement(s) of the sensed component(s).

A sensor system typically detects a characteristic of a sensed parameter which varies in relationship to the position of the one or more sensed elements within a sensed area. The sensed elements extend into or otherwise influence the sensed area in a manner that directly or indirectly affects the characteristic of the sensed parameter. The relative positions of the sensor and the sensed element affect the characteristics of the sensed parameter, allowing the controller of the sensor system to determine different positions of the sensed element.

Suitable sensor systems may include the combination of an active component and a passive component. With the sensing component operating as the active component, it is not necessary to have both components connected with other system elements such as a power supply or controller.

Any of a variety of sensing technologies may be incorporated by which the relative positions of two members can be detected. Such technologies may include, for example, technologies based on tactile, optical, inductive or electrical measurements.

Such technologies may include the measurement of a sensed parameter associated with a field, such as a magnetic field. In one form, a magnetic sensor senses the change in a sensed magnetic field as a magnetic component is moved relative to the sensor. In another embodiment, a sensor system may sense characteristics of and/or changes to a magnetic field as an object is positioned within and/or moved through the magnetic field. The alterations of the field change the characteristic of the sensed parameter in relation to the position of the sensed element in the sensed area. In such embodiments the sensed parameter may be a capacitance, conductance, resistance, impedance, voltage, inductance, etc. For example, a magneto-resistive type sensor detects the distortion of an applied magnetic field which results in a characteristic change in the resistance of an element of the sensor. As another example, Hall effect sensors detect changes in voltage resulting from distortions of an applied magnetic field.

In one aspect, the sensor system detects relative positions or movements of the sensed elements, and therefore of the associated members of the medication delivery device. The sensor system produces outputs representative of the position(s) or the amount of movement of the sensed component. For example, the sensor system may be operable to generate outputs by which the rotation of the dose setting member during dose delivery can be determined. A controller is operably connected to each sensor to receive the outputs. In one aspect, the controller is configured to determine from the outputs the amount of dose delivered by operation of the medication delivery device.

The dose delivery detection system involves detecting relative rotational movement between two members. With the extent of rotation having a known relationship to the amount of a delivered dose, the sensor system operates to detect the amount of angular movement from the start of a dose injection to the end of the dose injection. For example, a typical relationship for a pen injector is that an angular displacement of a dose setting member of 18° is the equivalent of one unit of dose, although other angular relationships are also suitable. The sensor system is operable to determine the total angular displacement of a dose setting member during dose delivery. Thus, if the angular displacement is 90°, then 5 units of dose have been delivered.

One approach for detecting the angular displacement is to count increments of dose amounts as the injection proceeds. For example, a sensor system may use a repeating pattern of sensed elements, such that each repetition is an indication of a predetermined degree of angular rotation. Conveniently, the pattern may be established such that each repetition corresponds to the minimum increment of dose that can be set with the medication delivery device.

An alternative approach is to detect the start and stop positions of the relatively moving member, and to determine the amount of delivered dose as the difference between those positions. In this approach, it may be a part of the determination that the sensor system detects the number of full rotations of the dose setting member. Various methods for this are well within the ordinary skill in the art, and may include "counting" the number of increments to assess the number of full rotations.

The sensor system components may be permanently or removably attached to the medication delivery device. In an illustrative embodiment, as least some of the dose detection system components are provided in the form of a module that is removably attached to the medication delivery device. This has the advantage of making these sensor components available for use on more than one pen injector.

In some embodiments, a sensing component is mounted to the actuator and a sensed component is attached to the dose setting member. The sensed component may also comprise the dose setting member or any portion thereof. The sensor system detects during dose delivery the relative rotation of the sensed component, and therefore of the dose setting member, from which is determined the amount of a dose delivered by the medication delivery device. In an illustrative embodiment, a rotation sensor is attached, and rotationally fixed, to the actuator. The actuator does not rotate relative to the body of the medication delivery device during dose delivery. In this embodiment, a sensed component is attached, and rotationally fixed, to the dose setting member, which rotates relative to the actuator and the device body during dose delivery. The sensed component may also comprise the dose setting member or any portion thereof. In an illustrative embodiment, the rotation sensor is not attached directly to the relatively rotating dose setting member during dose delivery.

Figure 5:
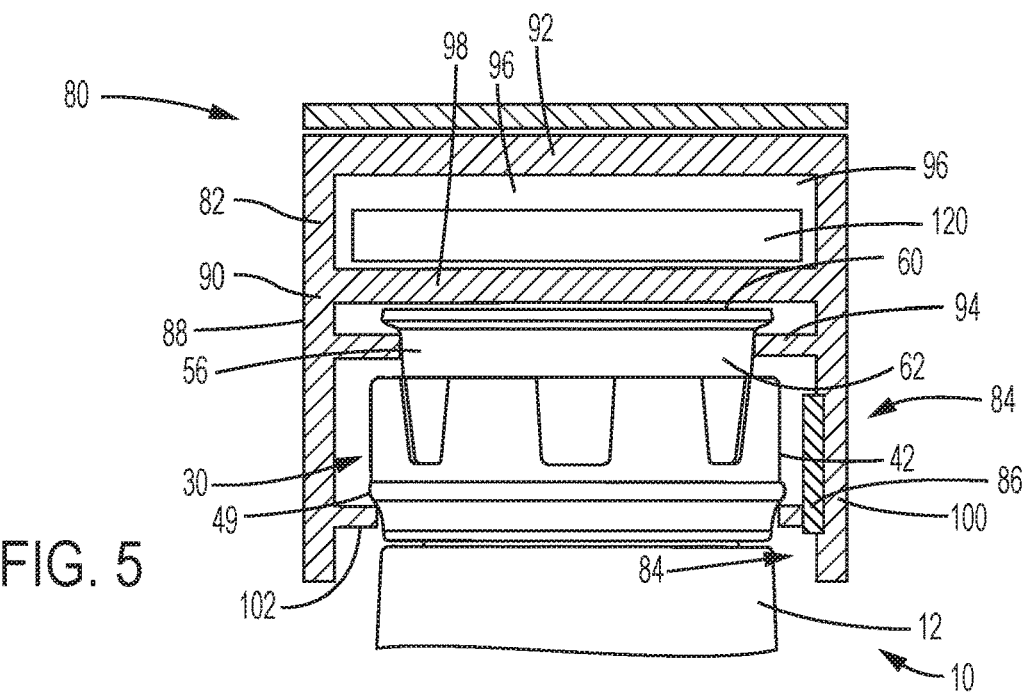
FIG. 5 is a side, diagrammatic view, partially in cross section, of a dose detection system module according to another exemplary embodiment attached to the proximal portion of a medication delivery device.

Referring to FIG. 5, there is shown in diagrammatic form a dose delivery detection system 80 including a module 82 useful in combination with a medication delivery device, such as device 10. Module 82 carries a sensor system, shown generally at 84, including a rotation sensor 86 and other associated components such as a processor, memory, battery, etc. Module 82 is provided as a separate component which may be removably attached to the actuator.

Dose detection module 82 includes a body 88 attached to dose button 56. Body 88 illustratively includes a cylindrical side wall 90 and a top wall 92, spanning over and sealing side wall 90. By way of example, in FIG. 5 upper side wall 90 is diagrammatically shown having inwardly-extending tabs 94 attaching module 82 to dose button 56. Dose detection module 82 may alternatively be attached to dose button 56 via any suitable fastening means, such as a snap or press fit, threaded interface, etc., provided that in one aspect module 82 may be removed from a first medication delivery device and thereafter attached to a second medication delivery device. The attachment may be at any location on dose button 56, provided that dose button 56 is able to move any required amount axially relative to dose setting member 30, as discussed herein.

During dose delivery, dose setting member 30 is free to rotate relative to dose button 56 and module 82. In the illustrative embodiment, module 82 is rotationally fixed with dose button 56 and does not rotate during dose delivery. This may be provided structurally, such as with tabs 94 of FIG. 5, or by having mutually-facing splines or other surface features on the module body 88 and dose button 56 engage upon axial movement of module 82 relative to dose button 56. In another embodiment, the distal pressing of the module provides a sufficient frictional engagement between module 82 and dose button 56 as to functionally cause the module 82 and dose button 56 to remain rotationally fixed together during dose delivery.

Top wall 92 is spaced apart from face 60 of dose button 56 and thereby provides a cavity 96 in which some or all of the rotation sensor and other components may be contained. Cavity 96 may be open at the bottom, or may be enclosed, such as by a bottom wall 98. Bottom wall 98 may be positioned in order to bear directly against face 60 of dose button 56. Alternatively, bottom wall 98 if present may be spaced apart from dose button 56 and other contacts between module 82 and dose button 56 may be used such that an axial force applied to module 82 is transferred to dose button 56. In another embodiment, module 82 may be rotationally fixed to the one-piece dose button 56' shown in FIG. 27.

In an alternate embodiment, module 82 during dose setting is instead attached to dose setting member 30. For example, side wall 90 may include a lower wall portion 100 having inward projections 102 that engage with skirt 42 in a position underneath ridge 49. In this approach, tabs 94 may be eliminated and module 82 effectively engages the proximal face 60 of dose button 56 and the distal side of annular ridge 49. In this configuration, lower wall portion 100 may be provided with surface features which engage with the surface features of skirt 42 to rotationally fix module 82 with skirt 42. Rotational forces applied to housing 82 during dose setting are thereby transferred to skirt 42 by virtue of the coupling of lower wall portion 100 with skirt 42.

Module 82 is disengaged rotationally from skirt 42 in order to proceed with dose delivery. The coupling of lower wall portion 100 with skirt 42 is configured to disconnect upon distal axial movement of module 82 relative to skirt 42, thereby allowing skirt 42 to rotate relative to module 82 during dose delivery.

In a similar fashion, module 82 may be coupled with both dose button 56 and skirt 42 during dose setting. This has the advantage of providing additional coupling surfaces during rotation of the module in dose setting. The coupling of the module 82 to the skirt 42 is then released prior to dose injection, such as by the axial movement of module 82 relative to skirt 42 as dose delivery is being initiated, thereby allowing dose setting member 30 to rotate relative to module 82 during dose delivery.

In certain embodiments, rotation sensor 86 is coupled to side wall 90 for detecting a sensed component. Lower wall portion 100 also serves to reduce the likelihood that a user's hand inadvertently applies drag to dose setting member 30 as it rotates relative to module 82 and housing 12 during dose delivery. Further, since dose button 56 is rotationally fixed to dose setting member 30 during dose setting, the side wall 90, including lower wall portion 100, provide a single, continuous surface which may be readily grasped and manipulated by the user during dose setting.

When the injection process is initiated by pressing down on the dose detection module 82, dose button 56 and dose setting member 30 are rotationally fixed together. Movement of module 82, and therefore dose button 56, a short distance, for example less than 2 mm, releases the rotational engagement and the dose setting member 30 rotates relative to module 82 as the dose is delivered. Whether by use of a finger pad or other triggering mechanism, the dose detection system is activated before the dose button 56 has moved a sufficient distance to disengage the rotational locking of the dose button 56 and the dose setting member 30.

Illustratively, the dose delivery detection system includes an electronics assembly suitable for operation of the sensor system as described herein. A controller is operably connected to the sensor system to receive outputs from one or more rotational sensors. The controller may include conventional components such as a processor, power supply, memory, microcontrollers, etc. contained for example in cavity 96 defined by module body 88. Alternatively, at least some components may be provided separately, such as by means of a computer, smart phone or other device. Means are then provided to operably connect the external controller components with the sensor system at appropriate times, such as by a wired or wireless connection.

An exemplary electronics assembly 120 comprises a flexible printed circuit board (FPCB) having a plurality of electronic components. The electronics assembly comprises a sensor system including one or more rotation sensors 86 operatively communicating with a processor for receiving signals from the sensor representative of the sensed relative rotation. The electronics assembly further includes a microcontroller unit (MCU) comprising at least one processing core and internal memory. The system includes a battery, illustratively a coin cell battery, for powering the components. The MCU includes control logic operative to perform the operations described herein, including detecting a dose delivered by medication delivery device 10 based on a detected rotation of the dose setting member relative to the actuator. In one embodiment, the detected rotation is between the skirt 42 and the dose button 56 of a pen injector.

The MCU is operative to store the detected dose in local memory (e.g., internal flash memory or on-board EEPROM). The MCU is further operative to wirelessly transmit and/or receive a signal representative of the detected dose to a paired remote electronic device, such as a user's smartphone, over a Bluetooth low energy (BLE) or other suitable short or long range wireless communication protocol. Illustratively, the BLE control logic and MCU are integrated on a same circuit.

Much of the sensing electronics is contained in the cavity 96. However, the rotation sensor may be positioned in a variety of locations in order to sense the relative movement of the sensed component. For example, the rotation sensor may be located within cavity 96, within body 88 but outside of the cavity 96, or in other locations of the body, such as on lower wall portion 100. The only requirement is that the rotation sensor be positioned to effectively detect the rotational movement of the sensed component during dose delivery. In some embodiments, the rotation sensor is integral to the device 10.

One or more sensed elements are attached to the dose setting member 30. In one aspect, the sensed elements are directly attached to skirt 42 of the dose setting member. Alternatively, sensed elements may be attached to any one or more of the dose setting components, including the dial member, flange and/or skirt. The only requirement is that the sensed element(s) be positioned to be sensed by the rotation sensor during relative rotational movement during dose delivery. In other embodiments, the sensed component comprises the dose setting member 30 or any portion thereof.

Figure 27:
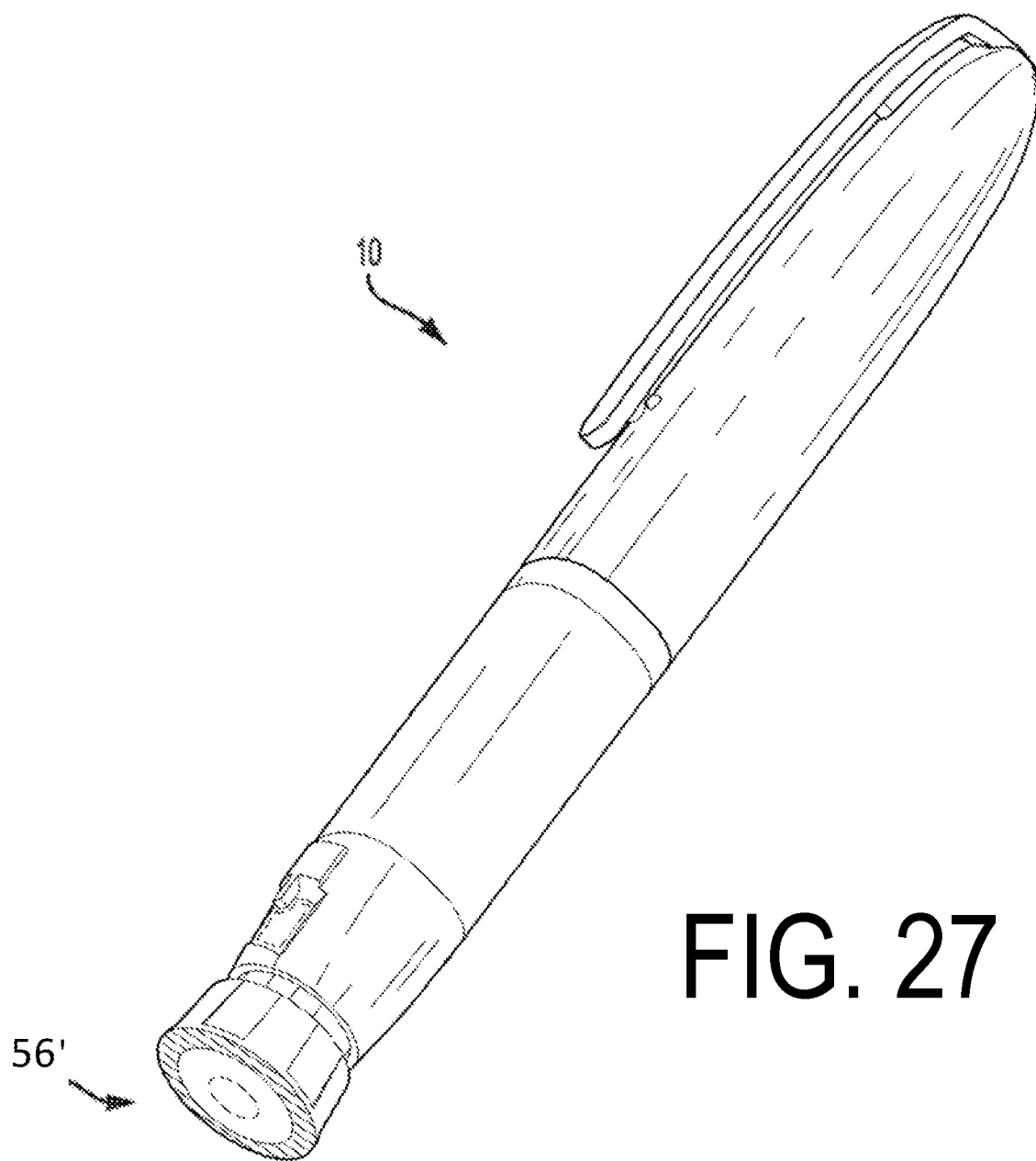
FIG. 27 is a perspective view of an exemplary medication delivery device of the present disclosure.

Further illustrative embodiments of a dose delivery detection system 80 are provided in FIGS. 6-13. The embodiments are shown in somewhat diagrammatic fashion, as common details have already been provided with respect to FIGS. 1-5. In general, each embodiment includes similar components of the dose detection module 82, including a body 88 having a cylindrical upper wall 90 and a top wall 92. Each embodiment also includes a lower wall 100, although it will be appreciated that variations on these components, including the absence of lower wall 100, are within the scope of the disclosure. Other parts common to the earlier descriptions herein include an electronics assembly 120 contained within cavity 96 of module body 88, dose button 56, dose setting member 32 and device housing 12. Further, in each embodiment the dose detection module 82 is diagrammatically shown as being attached to the annular side wall 62 of dose button 56, although alternative forms and locations of attachment may be used. For example, dose detection module 82 may be attached to dose button 56 and releasably attached to skirt 42 in some embodiments. Also, dose detection module 82 may be attached to one-piece dose button 56', as shown in FIG. 27.

Each example also demonstrates the use of a particular type of sensor system. However, in some embodiments the dose detection system includes multiple sensing systems using the same or different sensing technologies. This provides redundancy in the event of failure of one of the sensing systems. It also provides the ability to use a second sensing system to periodically verify that the first sensing system is performing appropriately.

Figure 6:
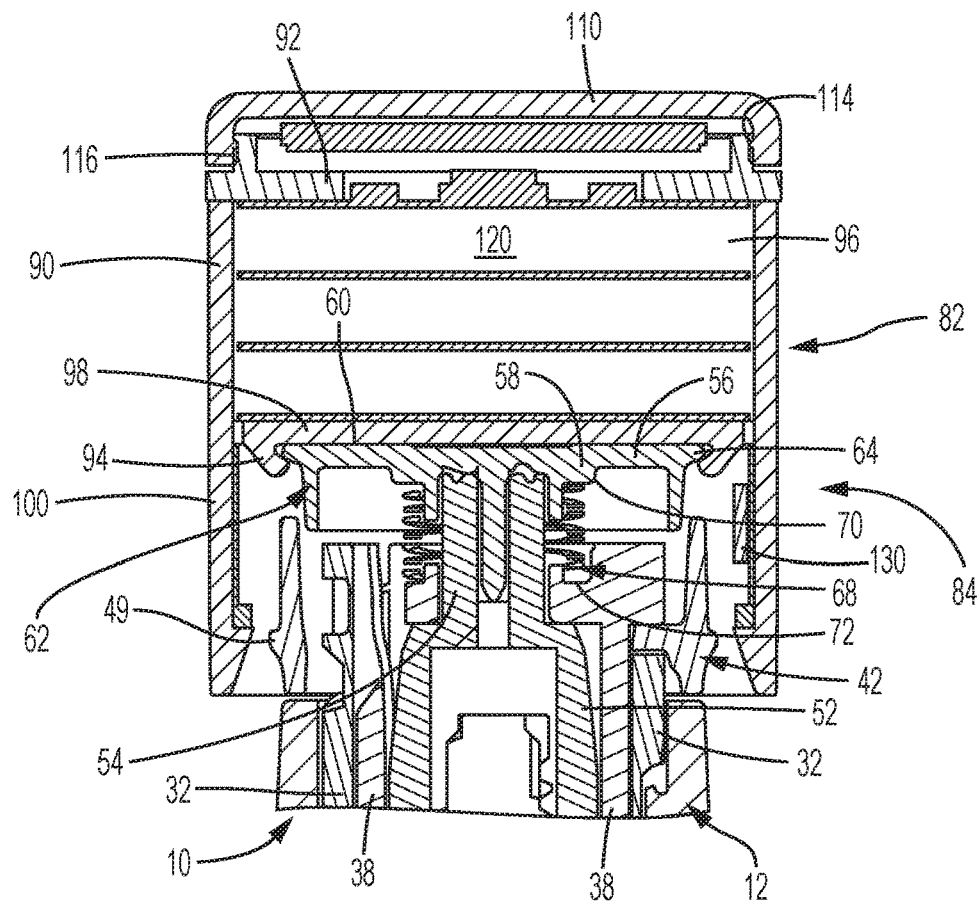
FIG. 6 is a cross-sectional view of a module of a dose delivery detection system according to an exemplary embodiment attached to the proximal portion of a medication delivery device.

In certain embodiments, as shown in FIG. 6, attached to top wall 92 of module 82 is a finger pad 110. Finger pad 110 is coupled to top wall 92, which is in turn attached to upper side wall 90. Finger pad 110 includes a ridge 114 which extends radially inward and is received within circumferential groove 116 of wall component 92. Groove 116 allows a slight axial movement between finger pad 110 and wall component 92. Springs (not shown) normally urge finger pad 110 upwardly away from wall component 92. Finger pad 110 may be rotationally fixed to wall component 92. Axial movement of finger pad 110 in the distal direction toward module body 88 as the injection process is initiated may be used to trigger selected events. One use of finger pad 110 may be the activation of the medication delivery device electronics upon initial pressing and axial movement of the finger pad 110 relative to the module body 88 when dose injection is initiated. For example, this initial axial movement may be used to "wake up" the device, and particularly the components associated with the dose detection system. In one example, module 82 includes a display for indication of information to a user. Such a display may be integrated with finger pad 110. MCU includes a display drive software module and control logic operative to receive and processed sensed data and to display information on said display, such as, for example, dose setting, dosed dispensed, status of injection, completion of injection, date and/or time, or time to next injection.

In the absence of a finger pad, the system electronics may be activated in various other ways. For example, the initial axial movement of module 82 at the start of dose delivery may be directly detected, such as by the closing of contacts or the physical engagement of a switch. It is also known to activate a medication delivery device based on various other actions, e.g., removal of the pen cap, detection of pen movement using an accelerometer, or the setting of the dose. In many approaches, the dose detection system is activated prior to the start of dose delivery.

Figure 7:
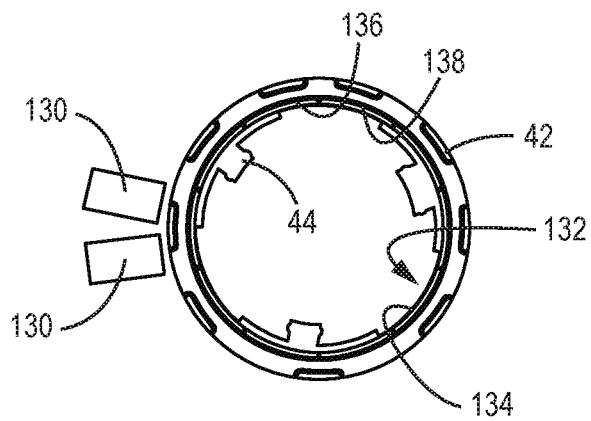
FIG. 7 is a top, diagrammatic view showing rotation sensors positioned to detect magnetic sensed elements attached to a dose setting member in accordance with an exemplary embodiment.
Figure 8:
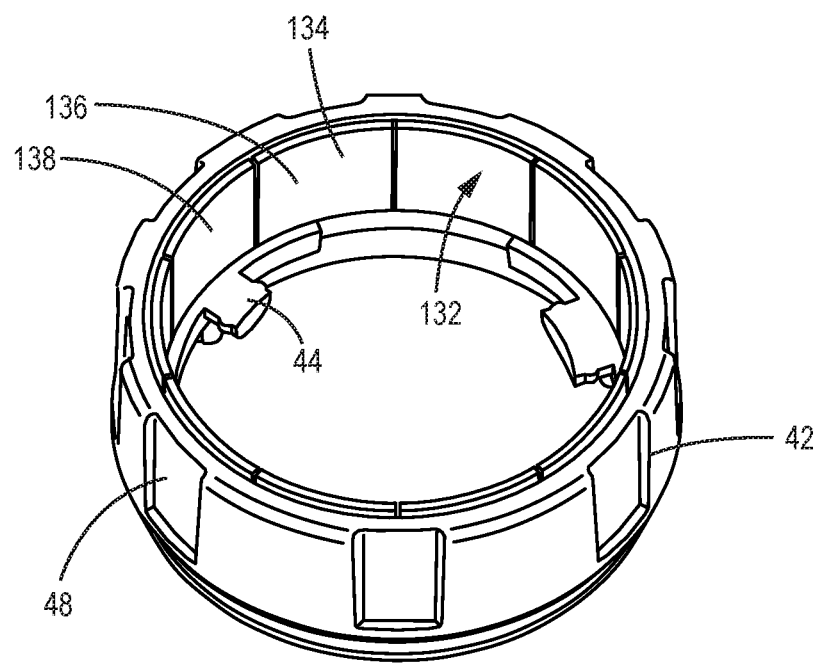
FIG. 8 is a perspective view of the dose setting member of FIG. 7 including the magnetic sensed elements.

Referring to FIGS. 6-8, dose detection module 82 operates using a magnetic sensing system 84. Two magnetic sensors 130 are positioned on lower wall portion 100 (illustratively the inside surface of lower wall portion 100) opposite skirt 42 of dose setting member 30. As for all embodiments, the number and location of the rotation sensor (s) and the sensed element(s) may be varied. For example, the embodiment of FIGS. 6-8 may instead include any number of magnetic sensors 130 evenly or unevenly spaced around skirt 42. The sensed component 132 (FIGS. 7 and 8) comprises a magnetic strip 134 secured to skirt 42, illustratively on the interior of skirt 42. In the illustrative embodiment, the strip comprises 5 pairs of north-south magnetic components, e.g., 136 and 138, each magnetic portion therefore extending for 36°. The magnetic sensors 130 are positioned at a separation of 18° (FIG. 7), and read the digital positions of magnetic strip 132, and therefore of skirt 42, in a 2-bit grey code fashion. For example, as the sensor detects the passage of a N-S magnetic pair, it is detected that skirt 42 has rotated 36°, corresponding to 2 units, for example, of dose being added (or subtracted).

Figure 9:
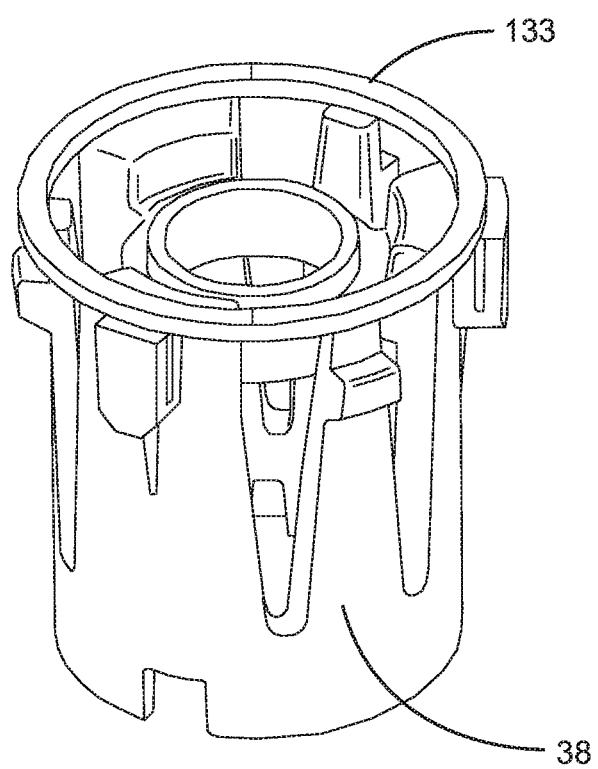
FIG. 9 is a perspective view of an alternate embodiment of a magnetic dose delivery detection system.

Other magnetic patterns, including different numbers or locations of magnetic elements, may also be used. Further, in an alternative embodiment, a sensed component 133 is attached to or integral with flange 38 of dose setting member 30, as illustrated in FIG. 9.

As previously described, the sensing system 84 is configured to detect the amount of rotation of the sensed element relative to the magnetic sensors 130. This amount of rotation is directly correlated to the amount of dose delivered by the device. The relative rotation is determined by detecting the movements of the skirt 42 during dose delivery, for example, by identifying the difference between the start and stop positions of skirt 42, or by "counting" the number of incremental movements of skirt 42 during the delivery of medication.

Figure 10A:
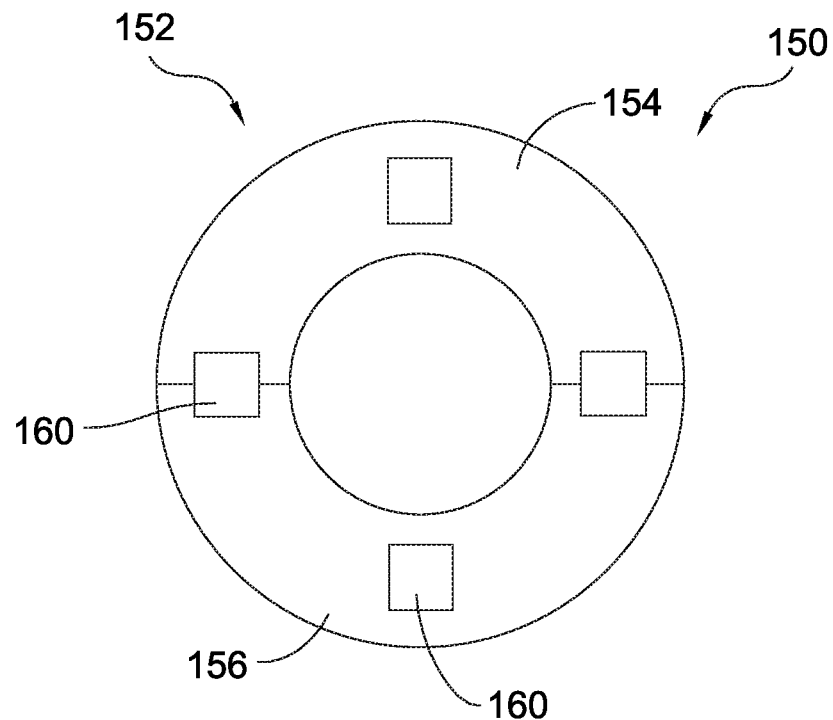
FIGS. 10A-B and 11A-B show yet other exemplary embodiments of dose delivery detection systems utilizing magnetic sensing.
Figure 10B:
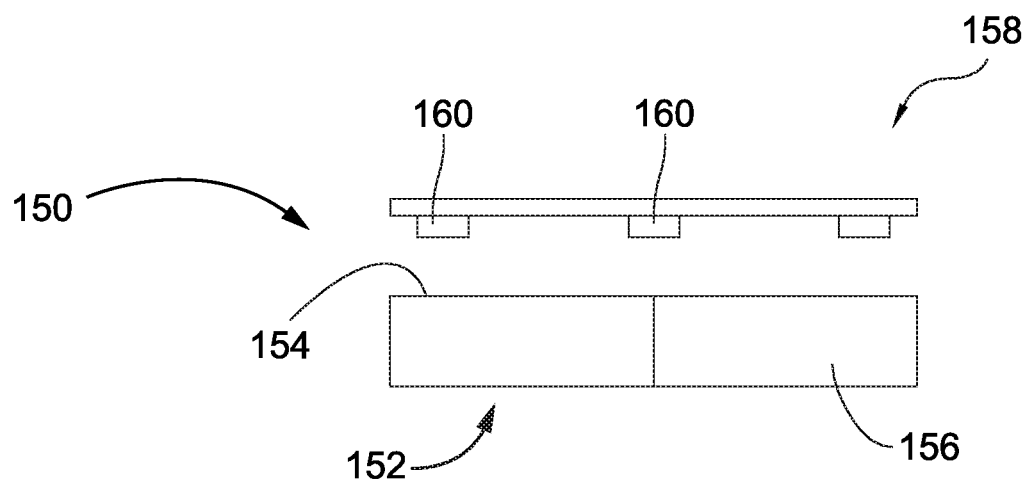

Referring to FIGS. 10-11, there is shown an exemplary magnetic sensor system 150 including as the sensed element an annular, ring-shaped, bipolar magnet 152 having a north pole 154 and a south pole 156. Magnet 152 is attached to flange 38 and therefore rotates with the flange during dose delivery. Magnet 152 may alternately be attached to dose dial 32 or other members rotationally fixed with the dose setting member.

Figure 11A:
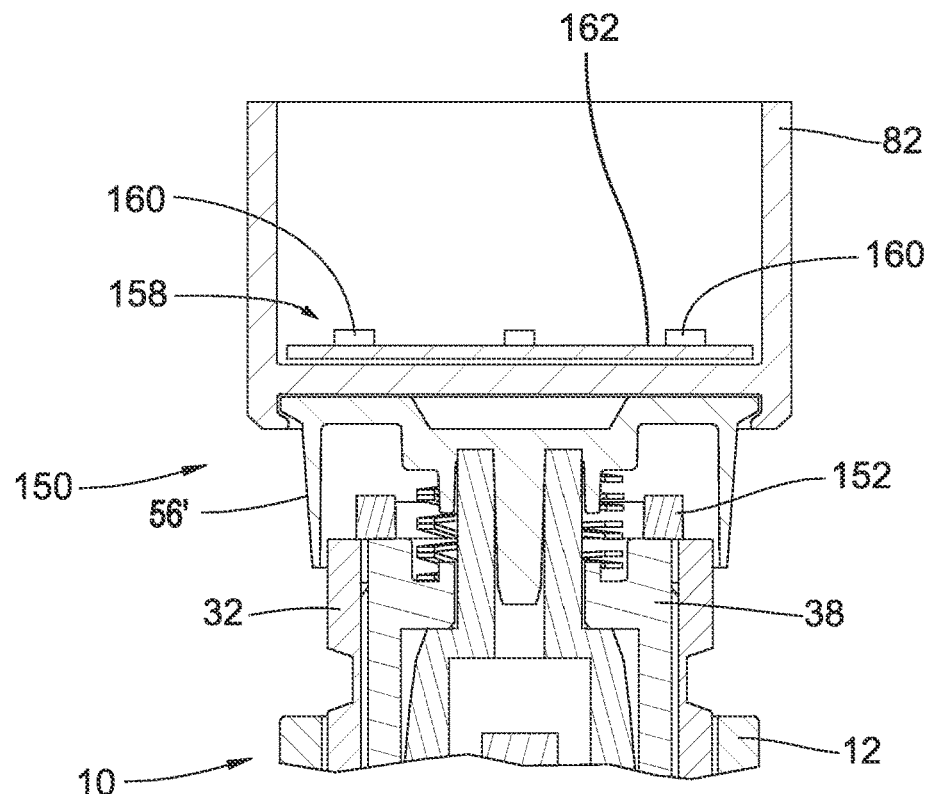

Sensor system 150 further includes a sensor 158 including one or more sensing elements 160 operatively connected with sensor electronics (not shown) contained within module 82. The sensing elements 160 of sensor 158 are shown in FIG. 11A attached to printed circuit board 162 which is turn attached module 82, which is rotationally fixed to dose button 56. Consequently, magnet 152 rotates relative to sensing elements 160 during dose delivery. Sensing elements 160 are operable to detect the relative angular position of magnet 152. Magnetic sensor system 150 thereby operates to detect the total rotation of flange 38 relative to dose button 56, and therefore the rotation relative to housing 12 during dose delivery.

Figure 11B:
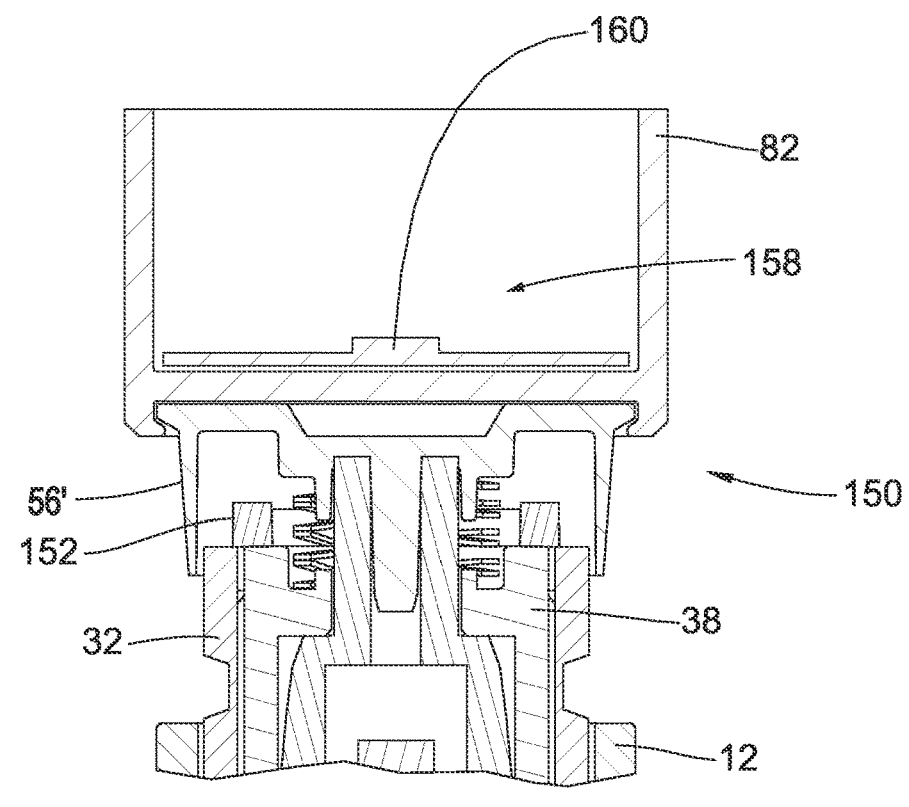

In one embodiment, magnetic sensor system 150 includes four sensing elements 160 equi-radially spaced within module 82. Alternative numbers and positions of the sensing elements may be used. For example, in another embodiment, shown in FIG. 11B, a single sensing element 160 is used. Further, sensing element 160 in FIG. 11B is shown centered within module 82, although other locations may also be used. In the foregoing embodiments, sensing elements 160 are shown attached within module 82. Alternatively, sensing elements 160 may be attached to any portion of a component rotationally fixed to dose button 56 such that the component does not rotate relative to housing 12 during dose delivery.

For purposes of illustration, magnet 152 is shown as a single, annular, bi-polar magnet attached to flange 38. However, alternative configurations and locations of magnet 152 are contemplated. For example, the magnet may comprise multiple poles, such as alternating north and south poles. In one embodiment the magnet comprises a number of pole pairs equaling the number of discrete rotational, dose-setting positions of flange 38. Magnet 152 may also comprise a number of separate magnet members. In addition, the magnet component may be attached to any portion of a member rotationally fixed to flange 38 during dose delivery, such as skirt 42 or dose dial member 32.

The sensor system is alternatively exemplified in FIGS. 12-13 as an inductive sensor system 170. Sensor system 170 utilizes a sensed element 171 comprising a metal band 172 attached to skirt 42 as the sensed element. Sensor system 170 further includes a sensor 174 comprising one or more sensing elements 176, such as the four independent antennas 178 equi-radially spaced along the circumference of skirt 42. These four antennas form two antenna pairs located 180 degrees apart and provide a ratio-metric measurement of the angular position of skirt 42.

Metal band 172 is shaped such that one or more distinct rotational positions of skirt 42 relative to module 82 may be detected. Metal band 172 has a shape which generates a varying signal upon rotation of skirt 42 relative to antenna 178. Illustratively, FIGS. 13A-C show a band pattern in which FIG. 13B shows a rotation of 90° from the position of FIG. 13A, and FIG. 13C shows an additional 90° rotation. This pattern generates a detected sine wave response upon rotation of skirt 42 relative to module 82, as shown diagrammatically in FIG. 12D, in which positions a-d correlate to those shown in FIG. 12A.

FIG. 13D provides a schematic showing inductive sensor system 170 incorporated into module 82 and skirt 42 of pen 10. Metal band 172 is shown attached to skirt 42. Antennas 178 are operably connected with electronics 120 such that the antennas function to detect positions of skirt 42 relative to module 82, and therefore relative to housing 12 of pen 10, during dose delivery.

In the embodiment shown in FIGS. 12-13, inductive sensor system 170 includes four sensing elements 176 comprising equi-radially spaced antennas 178 within module 82. Alternative numbers and positions of the sensing elements may be used. For example, another embodiment utilizes a single antenna. In the illustrated embodiment, antennas 178 are shown attached within module 82. Alternatively, the antenna(s) may be attached to any portion of a component rotationally fixed to dose button 56 such that the component does not rotate relative to housing 12 during dose delivery.

For purposes of illustration, metal band 172 is shown as a single, cylindrical band attached to the exterior of skirt 42. However, alternate configurations and locations of metal band 172 are contemplated. For example, the metal band may comprise multiple discrete metal elements. In one embodiment the metal band comprises a number of elements equal to the number of discrete rotational, dose-setting positions of skirt 42. The metal band in the alternative may be attached to any portion of a component rotationally fixed to skirt 42 during dose delivery, such as flange 38 or dial member 32. The metal band may comprise a metal element attached to the rotating member on the inside or the outside of the member, or it may be incorporated into such member, as by metallic particles incorporated in the component, or by over-molding the component with the metal band.

Figure 12A:
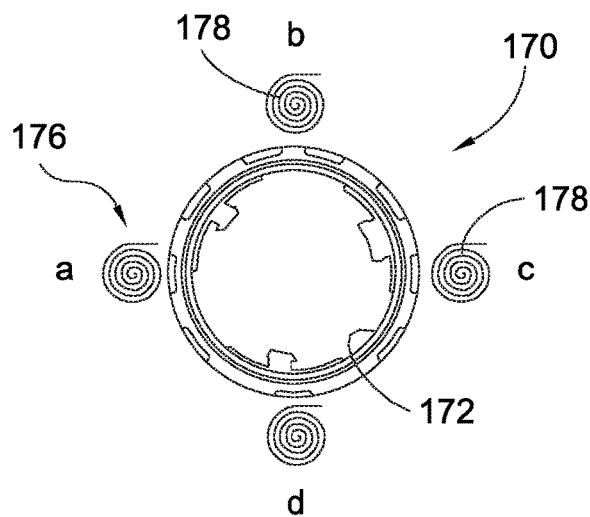
Figure 12B:
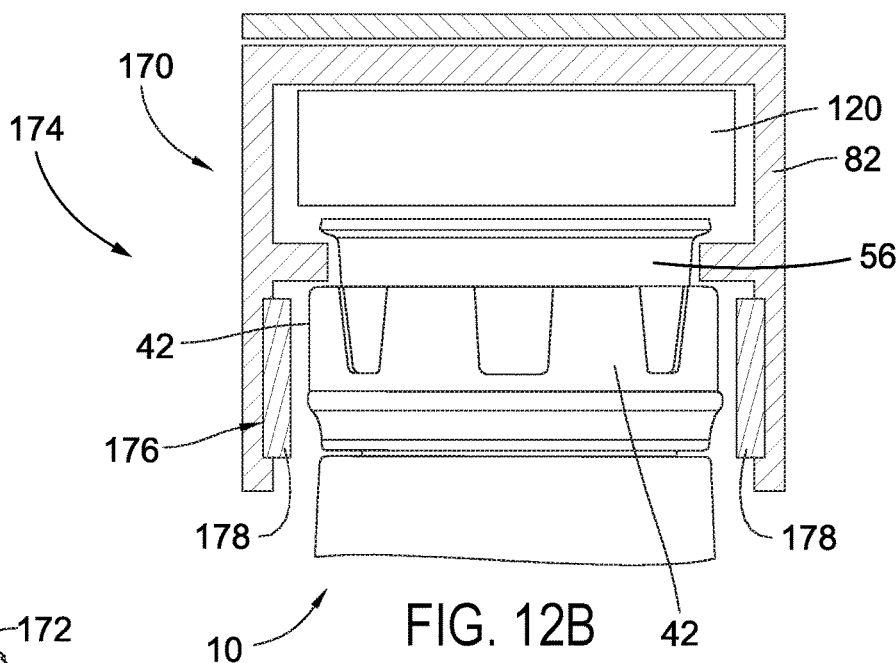
Figure 12C:
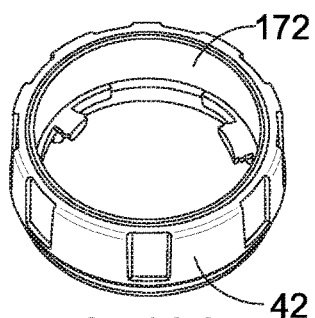
Figure 12D:
Figure 13E:
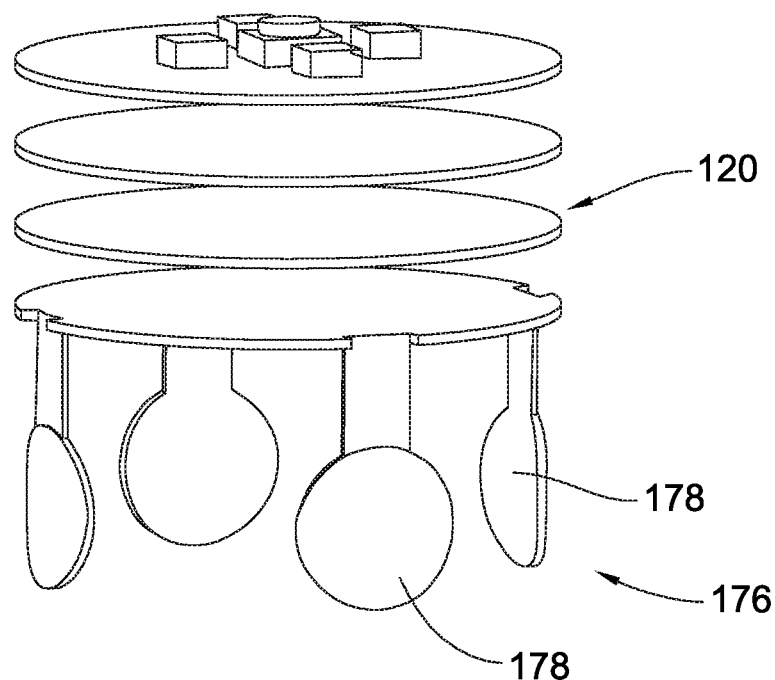
Figure 13F:
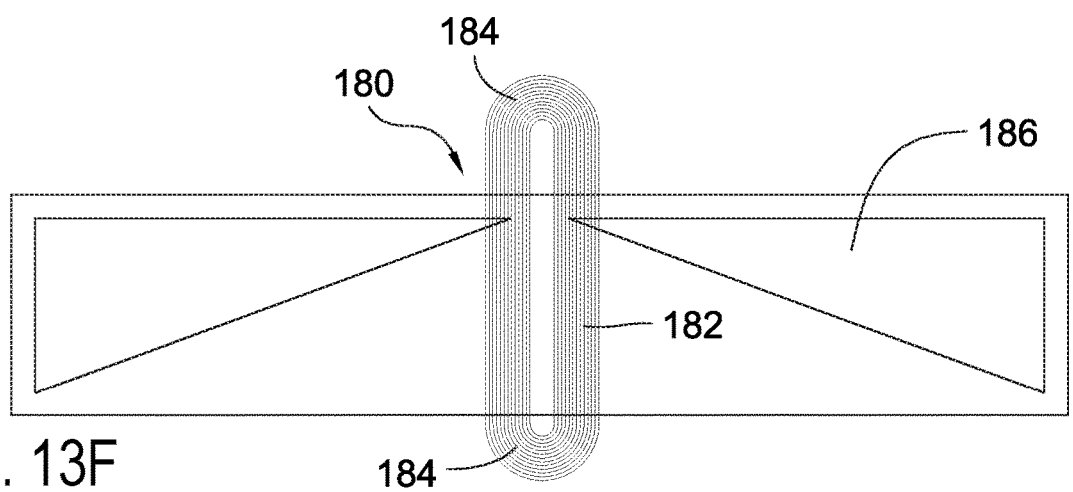
Figure 13G:
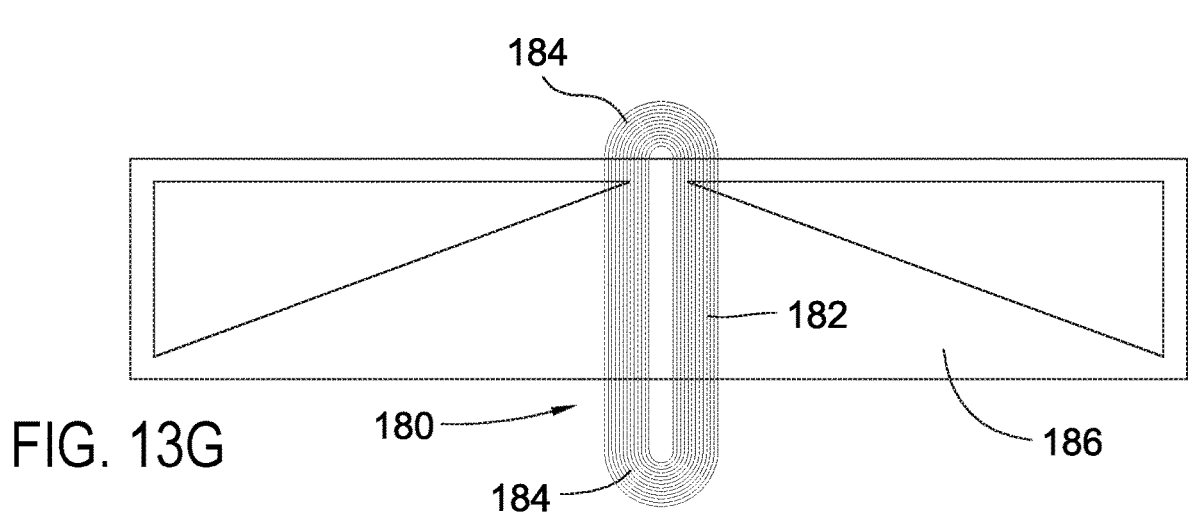

The antennas 178 are shown schematically in FIG. 12A and structurally in FIGS. 13D and 13E as being round. An alternate configuration of the antennas is shown schematically in FIGS. 13F and 13G. Shown in FIG. 13F is an "elongated antenna" 180 having a rectangular midsection 182 and semi-circular ends 184. FIG. 13F depicts the position of antenna 180 relative to metal band 186. This position corresponds to the pen injector being at rest with no axial displacement of the module as in delivering a dose. In FIG. 13G, antenna 180 is in the position corresponding to the module having been pressed to cause delivery of a dose. The module and therefore antenna 180 has been displaced, downward in FIG. 13G, relative to metal band 186. It is apparent that the elongated antenna 180 may provide a more uniform sensing of metal band 186 as there is a more constant area of midsection 182 overlapping with the metal band.

In one aspect, there is disclosed a modular form of the dose detection system. The use of a removably attached module is particularly adapted to use with a medication delivery device in which the actuator and the dose setting member both include portions external to the medication device housing. These external portions allow for direct attachment of the sensing component to the actuator, such as a dose button, and a sensed component to a dose setting member, such as a dose skirt, flange, or dial member, as described herein. In this regard, a "dose button" is used to refer more generally to a component of a medication delivery device which includes a portion located outside of the device housing and includes an exposed surface available for the user to use in order to deliver a set dose. Similarly, a dose "skirt" refers more generally to a component of a medication delivery device which is located outside of the device housing and which thereby has an exposed portion available for the user to grasp and turn the component in order to set a dose. As disclosed herein, the dose skirt rotates relative to the dose button during dose delivery. Also, the dose skirt may be rotationally fixed to the dose button during dose setting, such that either the dose skirt or dose button may be rotated to set a dose. In an alternative embodiment, the delivery device may not include a dose skirt, and a user may grasp and rotate the actuator (e.g., dose button) for dose setting. In some embodiments, with a dose detection module attached to the actuator and/or the dose skirt, the dose detection module may be rotated to thereby rotate the dose setting member of the delivery device to set a dose to be delivered.

It is a further feature of the present disclosure that the sensing system of dose detection system 80 may be originally incorporated into a medication delivery device as an integrated system rather than as an add-on module.

The foregoing provides a discussion of various structures and methods for sensing the relative rotation of the dose setting member relative to the actuator during dose delivery. In certain embodiments of medication delivery devices, the actuator moves in a spiral fashion relative to the pen body during dose setting. For illustrative purposes, this disclosure describes the dose detection system in respect to such a spiraling actuator. It will be appreciated by those skilled in the art, however, that the principles and physical operation of the disclosed dose detection system may also be used in combination with an actuator that rotates, but does not translate, during dose delivery. It will also be understood that the dose detection system is operable with other configurations of medical delivery devices provided that the device includes an actuator which rotates relative to a dose setting member during dose injection.

Detection systems may also be employed with the module for identifying a characteristic of the drug to be administered by a pen injector. Pen injectors are used with a wide variety of drugs, and even with various types of a given drug. For example, insulin is available in different forms depending on the intended purpose. Insulin types include rapid-acting, short-acting, intermediate-acting and long-acting. In another respect, the type of the drug refers to which drug is involved, e.g., insulin versus a non-insulin medication, and/or to a concentration of a drug. It is important not to confuse the type of drug as the consequences may have serious implications.

It is possible to correlate certain parameters based on the type of a drug. Using insulin as an example, there are known limitations as to the appropriate amount of a dose based on factors such as which type of insulin is involved, how the type of insulin correlates to the timing of the dose, etc. In another respect, it is necessary to know which type of drug was administered in order to accurately monitor and evaluate a treatment method. In one aspect, there is provided a sensor system which is capable of differentiating the type of drug that is to be administered.

For determining the drug type, a module is provided which detects a unique identification of the type of drug contained in the medication delivery device. Upon mounting the module to the medication delivery device, e.g., pen injector, the module detects the type of drug and stores it in memory. The module is thereafter able to evaluate a drug setting or delivery in view of the type of drug in the pen, as well as previous dosing history and other information.

Figure 14:
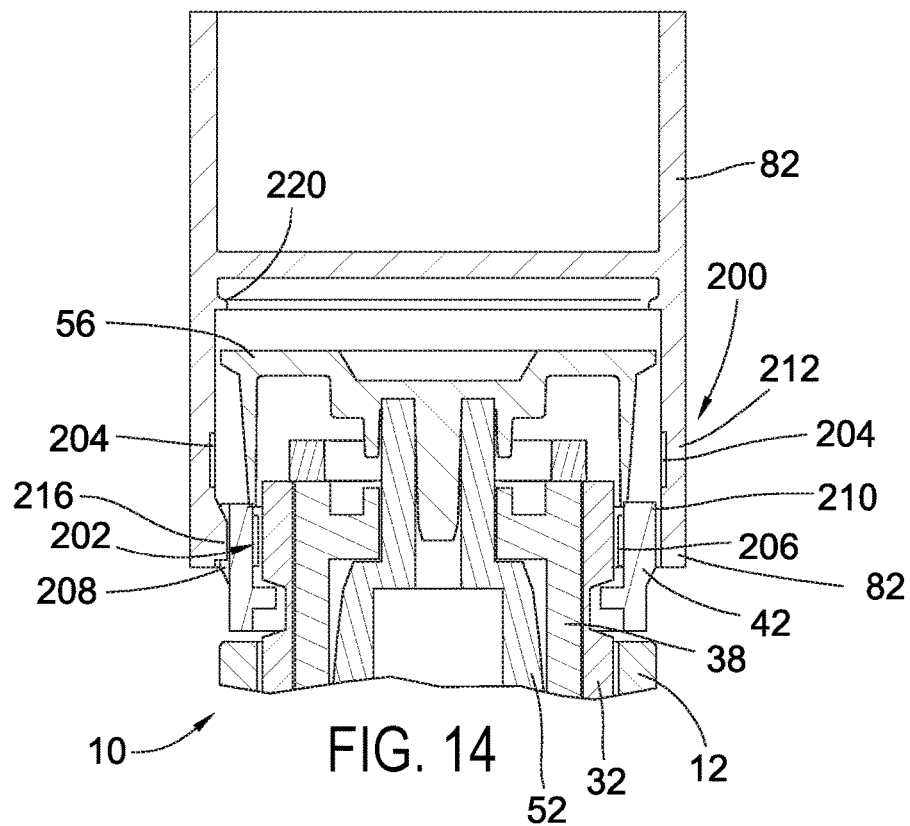
FIGS. 14-17 show an exemplary embodiment of a keying system useful with a dose type delivery system.

Referring to FIG. 14, pen injector 10 includes a sensor system 200 comprising a sensed component 202 and a sensing component 204. Sensor system 200 is operable to identify distinct angular orientation of sensed component 202 relative to pen injector 10. Sensor system 200 may be of any type, such as previously described, whereby specific angular positions can be identified.

In FIG. 14 there is shown a pen injector 10 including a housing 12, dose dial member 32, flange 38, clutch 52, dose button 56 and module 82. Sensed component 202 comprises one or more sensed elements 206 attached to pen injector 10 in a manner which is uniquely identifiable. By way of example, sensed elements 206 are shown attached to skirt 42 and always have the same orientation relative to skirt 42. Skirt 42 is rotatable relative to housing 12, but has a unique, identifiable position relative to housing 12 when in the "initial zero position" before any drug has been dispensed from the pen injector. Similarly, the sensed elements 206 may be attached to other rotatable members of the pen which have a uniquely identifiable position at a relevant time, such as during mounting of module 82 to pen injector 10. In this respect, sensed elements 206 may alternatively be attached, for example, to flange 38 or dial member 32.

Figure 15:
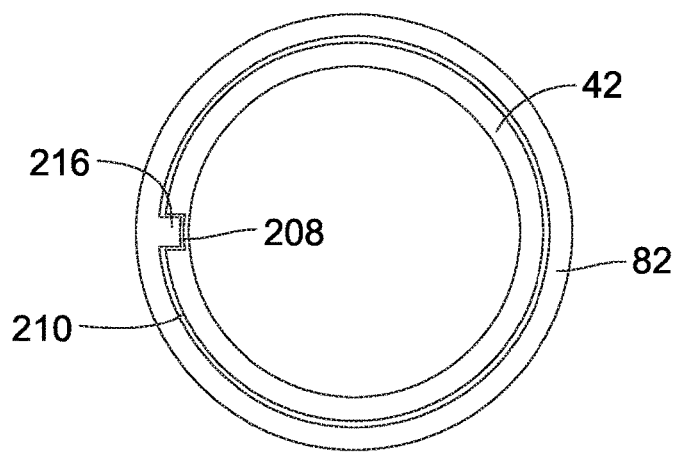

Skirt 42 includes a slot 208 (FIG. 15) extending axially on the outside of cylindrical skirt wall 210. The angular position of slot 208 relative to the angular position of sensed elements 206 is predetermined to correspond with a selected type of drug. Referring to FIG. 15, slot 208 is shown in the 9 o'clock position with skirt 42 at its initial, zero dose position. This position of slot 208 is assigned to represent a drug of a particular type. Alternatively, slot 208 is located in a different angular position for the initial, zero dose position, such as at the 3 o'clock position in FIG. 15. This position is then assigned to represent a drug of a second type. Detection of the position of the sensed elements 206 relative to slot 208 is therefore useful to identify the drug type contained by the pen injector 10.

Figure 16:
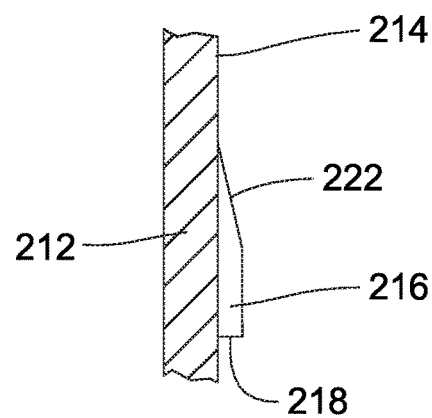

Module 82 includes a lower wall 212 including an inner surface 214 (FIG. 16). A tab 216 extends radially-inward of inner surface 214 and is configured to be received within slot 208. This condition is shown diagrammatically in FIG. 15. Tab 216 may be a simple projection of the inner surface, or may be provided as an arm able to flex radially-outwardly. In order to mount module 82 onto device 10, tab 216 is aligned with slot 208 and the module is then advanced in the direction of the device. Tab 216 is configured to assure proper alignment with slot 208 by having a blunt front end 218. This is provided to require tab 216 to be received within slot 208, rather than improperly riding over another location on the skirt.

Figure 17:
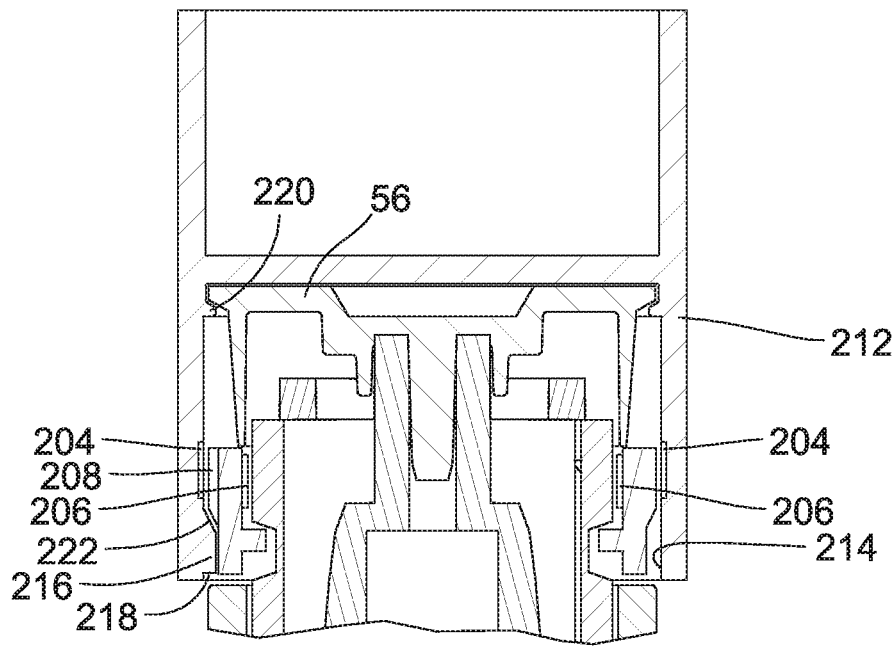

FIG. 14 shows the module during installation with tab 216 received within slot 208. In FIG. 17, module 82 has advanced to its installed position with tab 216 having moved out of slot 208. In this position, module 82 may be secured to dose button 56, for example by projection 220, as previously described. Positioning tab 216 outside of slot 208 allows for relative rotation between skirt 42 and module 82 after installation.

The identification of the drug type results from the predetermined orientation of the sensed elements relative to slot 208. For the embodiment of FIGS. 14-17, this means that the sensed elements are selectively positioned on skirt 42 to represent the type of drug. In that manner, whenever tab 216 is aligned with slot 208, the sensor system is operable to identify the relative angular relationship of the sensed element(s) and the module, and to derive the drug type therefrom. This detection may occur at any time that the tab and slot are aligned. Since this alignment is required at the time of mounting the module to the skirt, it is convenient to detect the position at this time. This may be caused by triggering the sensor system in any suitable manner, such as by proximity sensors, sliding contacts, a spring biased switch, or by manual activation upon beginning installation of the module.

Once the module has been installed and the type of drug identified, the pen injector is ready for use. When desired, module 82 is removed from the pen injector and is available for use on another pen injector. During operation, the delivery of a dose will rotate skirt 42 relative to module 82 such that at the end of a dose delivery the tab and slot may not be aligned. This is of no consequence to the operation of the pen injector as the tab is axially displaced from slot 208 and may therefore be in any angular position relative to skirt 42. However, to facilitate removal of module 82, tab 216 includes a tapered back end 222. This allows tab 216 to readily ride up over the outer surface 210 of skirt 42, regardless of the angular position of the skirt. The identification of drug type has been described using a tab and slot alignment mechanism. However, other alignment structures or systems are also contemplated.

This drug type detection is useful with a variety of sensor systems which are operable to detect a predetermined angular position of sensed elements relative to an alignment feature. These sensor systems include those previously disclosed herein. It is a further aspect that this drug type determination is readily combined with sensor systems for detecting the amount of a dose delivery. The two systems may operate independently or in concert with one another.

In a particular aspect, the sensor system used for detecting dose delivery is also used to identify the drug type. For example, FIGS. 10-11 and related text describe a magnetic sensor system which includes sensing elements 160 and a magnet 152 to determine the amount of a delivered dose. Magnet 152 has a unique configuration such that the sensor system is able to detect specific angular positions of magnet 152 relative to the sensing elements. This same sensor system therefore may be used in combination with an alignment feature, as described with respect to FIGS. 14-17, to identify the drug type contained by the pen injector. The inductive sensor system of FIGS. 12-13 is another example of a sensor system useful for determining both drug type and dose delivery.

Referring to FIGS. 18-21, an alternative drug and/or pen type detection system 230 is provided. In this embodiment, sensor system 230 is provided in connection with a module 232. Module 232 is removably attached to pen injector 10 in the same keyed manner as described with respect to module 82 in the embodiment of FIGS. 14-17. Sensor system 230 comprises a sensed component 234 and a sensor 236. Sensor system 230 is operable to identify distinct angular orientations of sensed component 234 relative to pen injector 10. The identification of the drug and/or pen type results from the predetermined orientation of the sensed element(s), as previously described. The sensor system is operable to identify the relative angular relationship of the sensed element(s) to the module, and to derive the medication and/or pen type therefrom.

Figure 19:
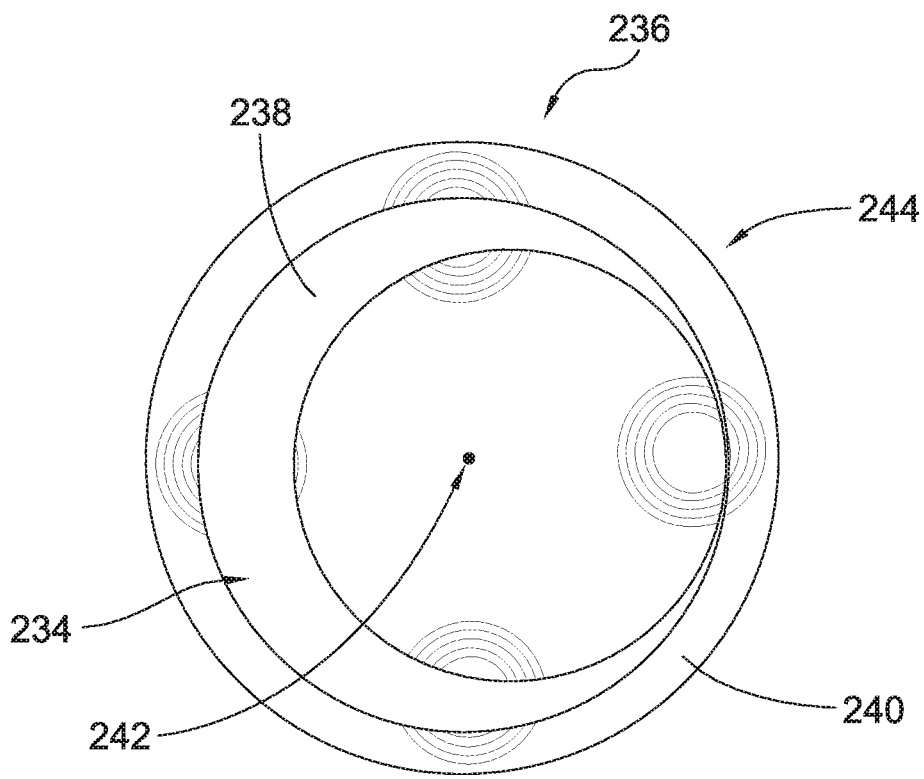
FIG. 19 is a diagrammatic view showing the positioning of a sensor and sensed component useful in an exemplary embodiment of a dose detection system.

The angular position of sensed component 234 is detected based on the unique angular profile of the sensed component. The term "unique angular profile" is used to identify a configuration of the sensed component in which the one or more sensed elements 238 comprising sensed component 234 enable the angular position of the sensed component to be uniquely identified for any predetermined angular position to be used by the system. A sensed component having such a unique angular profile is demonstrated in FIGS. 19-21. FIG. 19 shows diagrammatically the relationship between one embodiment of sensed component 234 and sensor 236. Sensed component 234 comprises a single sensed element 238 formed in a generally circular pattern.

Figure 20:
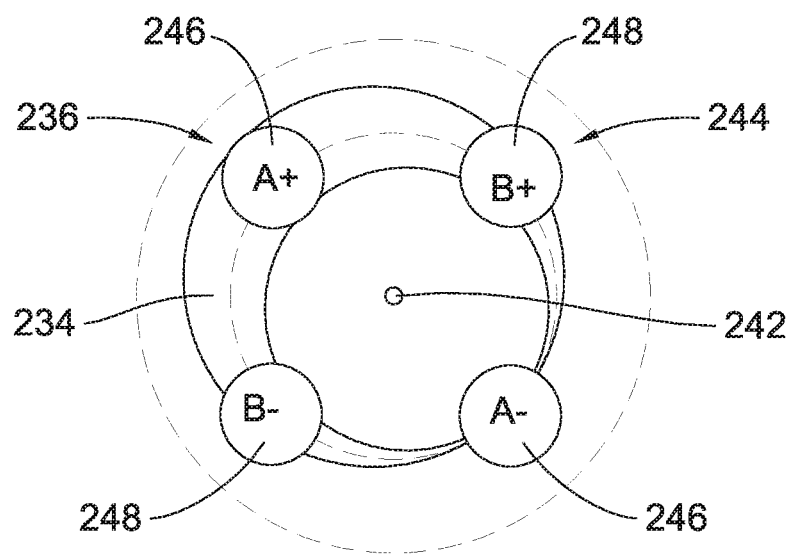
FIG. 20 is a schematic view showing the dose detection system of FIG. 19.

Sensor 236 is shown in FIG. 20 as comprising opposed pairs of inductive coil antennas 246 and 248, equi-radially positioned about the axis of rotation 242 of actuator 244. The antennas represent A+/A− and a B+/B− pairings. Sensed component 234 is positioned as shown in FIG. 20 configured to rotate around the axis of rotation 242. AC current flows through the paired antennas 246 and 248 generating four separate and independent AC magnetic fields.

Figure 21:
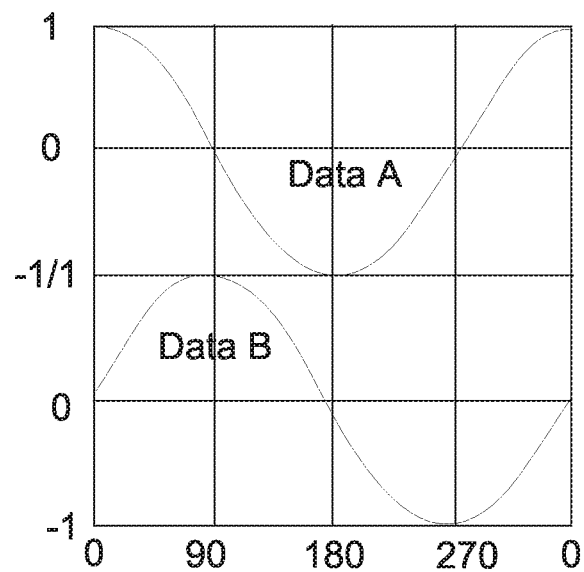
FIG. 21 is a graph showing the output responses for the dose detection system of FIG. 19.

As sensed element 234 passes by the antenna pairs, the magnetic fields of each antenna induce a circulating current (eddy current) on the surface of the metal in sensed element 234. This eddy current causes its own magnetic field, which opposes the original field generated by the antennas. As the metal of sensed element 234 moves closer to the antenna coils, a greater portion of the electromagnetic field produced by that coil is intercepted, and a lesser portion of the electromagnetic fields of the other antennas is intercepted. This means the eddy current increases as more electromagnetic field flux lines are intercepted, and decreases as fewer flux lines are intercepted of other coils. This change in the eddy currents in each of the antennas changes the effective inductance of each individual antenna. The system can measure these changes in the inductance of each antenna 246 and 248 over time and use that data from opposing coils 246 and 248 to cancel unwanted variances due to temperature or mechanical tolerances. The result is two continuously changing wave forms 90 degrees out of phase as shown in FIG. 21.

The corresponding levels of the two output signals can be then correlated to the various rotational positions of sensed component 234 relative to sensor 236 which allows for quadrature rotational sensing. The system provides response Data A and Data B from the A and B antenna pairings 246 and 248, respectively. Sensor system 230 is shown in FIG. 20 in the "0-position". From the shape of sensed component 234 and from the signal outputs, it is apparent that each relative rotational position of sensed component 234 has a unique signature of response, and thus the sensed component has a unique angular profile about axis of rotation 242 of actuator 244.

The output signals are processed and decoded to produce the unique signature for a given position of sensed element 234. Such processing may include signal processing to repeatedly sample the output or to convert the analog signals shown in FIG. 21 into separate digital square waves also 90 degrees out of phase. Lookup tables may be used to compare the current and previous positional information to decode the direction of movement. For example, if the last decoded value for the output signals A and B were 00 respectively, and the current value is 01, it may be said that the sensed element has moved one half step in the clockwise direction. The number of degrees for a given "step" is determined by the sampling rate of the analog signal. Increasing the sampling rate results in increased rotational resolution as smaller changes in angular position are detected. For detecting drug or device type, however, it is sufficient if the sensed component results in a unique signal output for any angular position which is correlated to a drug or device type, or any other information to be detected.

Sensor system 230 is configured to detect one or more angular positions of sensed component 234 relative to sensor 236. A controller 250 responsive to the one or more detected angular positions, and is thereby operable to determine information concerning the medication delivery device 10.

Figure 18:
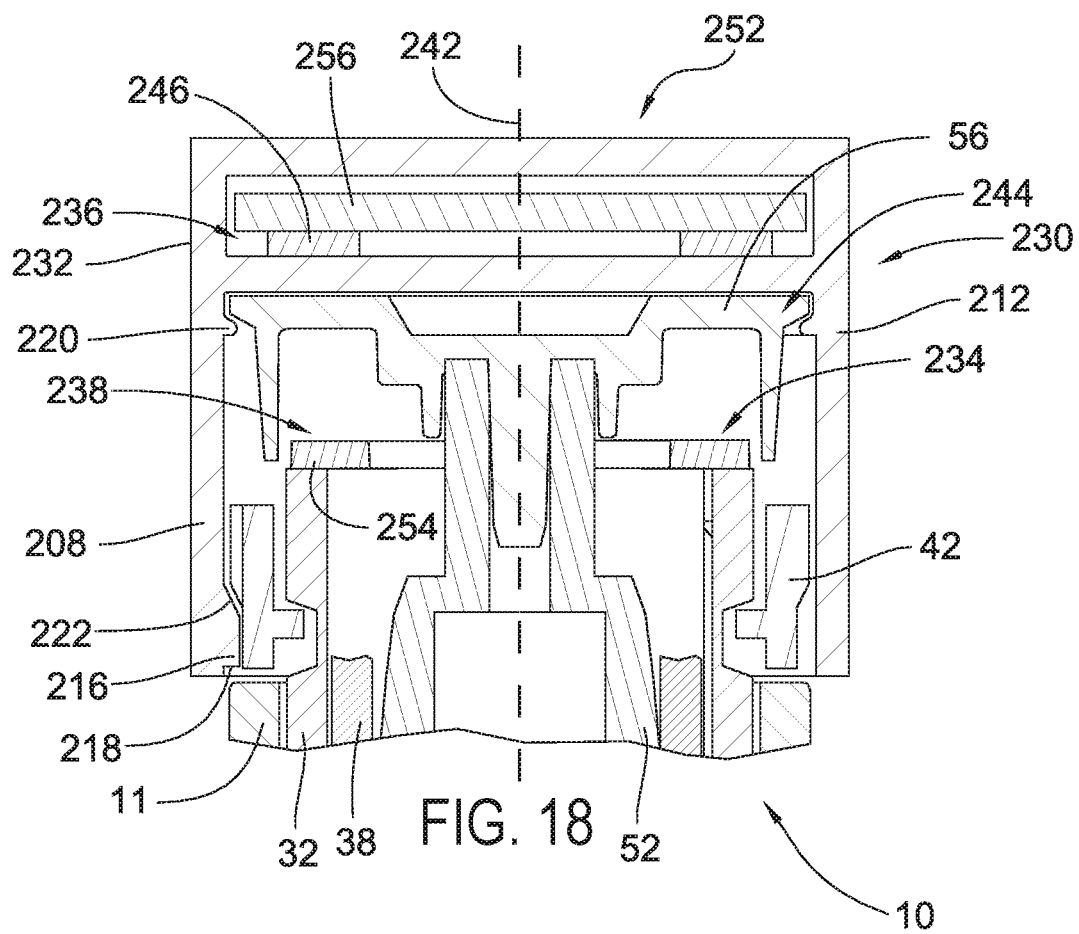
FIG. 18 is a cross-sectional view of a module of a dose detection system according to another embodiment, shown attached to the proximal portion of a medication delivery device.

In this illustrative embodiment, module 232 is attached to actuator 244 in a keyed relationship placing module 232, and therefore sensor 236, in a predetermined angular position relative to actuator 244. This keyed relationship, for example, may be provided in the same manner as for the embodiment of FIGS. 14-17, by having slot 208 of skirt 42 receiving tab 216 of module 232 (FIG. 18).

The predetermined angular position of module 232 is correlated to the type of medication delivery device 10, and/or the type of medication contained by medication delivery device 10. For example, the 0°-position shown in FIG. 20 may indicate that the pen injector is a pen having a particular capacity for medication, and the 90°-position may indicate that the medication is a fast-acting insulin. The 180° position may indicate, for example, that the medication delivery device is a pen injector containing a certain volume of fast-acting insulin. The correlations may be stored in memory carried by module 232. The controller is configured to determine the angular position of sensed component 234 relative to sensor 236 contained by module 232, and to derive the correlated information about the medication delivery device.

In another illustrative embodiment, sensor system 230 is operable to determine the amount of medication delivered by the medication delivery device. In accordance with this embodiment, the medication delivery device includes a dose setting member which rotates relative to the body of the medication delivery device during dose delivery. An actuator is axially and rotatably fixed with the dose setting member in a first operating mode during dose setting. The actuator is non-rotatable relative to the device body in a second operating mode during dose delivery. Sensor system 230 detects the rotation of the sensed component relative to the module during dose delivery, and the controller derives the amount of medication delivered.

In a further embodiment, the sensor system of the medication delivery device is operable to determine both information concerning the medication delivery device itself, and the amount of medication delivered by the medication delivery device. In this embodiment, module 232 is attached to the medication delivery device and sensor system 230 detects the angular position of sensed component 234 to module 232. This position is correlated to the type of medication delivery device, the type of medication contained by the medication delivery device, or any other desired information. The medication delivery device is then used to deliver a medication. During delivery, sensor system 230 detects the rotation of sensed component 234 relative to sensor 236 as an indication of the amount of medication delivered.

Referring to FIG. 18, further exemplary details of medication delivery system 252 are provided. System 252 comprises medication delivery device 10 including device body 11, dose dial member 32, flange 38, skirt 42, clutch 52 and dose button 56 in FIG. 18. Module 232 may be attached to dose button 56 by projections 220 extending inwardly from module 232. With initial attachment, module 232 is oriented with respect to skirt 42 by tab 216 being received within slot 208. In this orientation, the position of sensed component 234 relative to sensor 236 is correlated with the type of medication and/or the type of medication delivery device, as previously described.

For dose delivery, module 232 and dose button 56 are advanced in the distal direction with respect to skirt 42, to the position of FIG. 21. In this position, skirt 42, dose dial member 32 and flange 38 move together in rotation relative to dose button 56 as a dose of medication is delivered.

Sensed component 234 as shown comprises a single sensed element provided as a metal band 254. As described with respect to FIGS. 19-21, metal band 254 has a unique angular profile surrounding the axis of rotation 242. By way of example, sensed element 238 is shown attached to dose dial member 32. Dose dial member 32 is rotatable relative to device body 11, but has a unique, identifiable position relative to device body 11 when in the "initial zero position" before any drug has been dispensed from the medication delivery device. Similarly, sensed element 238 may be attached to other rotatable members of the medication delivery device which have a uniquely identifiable position at a relevant time, such as during mounting of module 232 to medication delivery device 10. In this respect, sensed component 234 may alternatively be attached, for example, to flange 38 or skirt 42.

Figure 22:
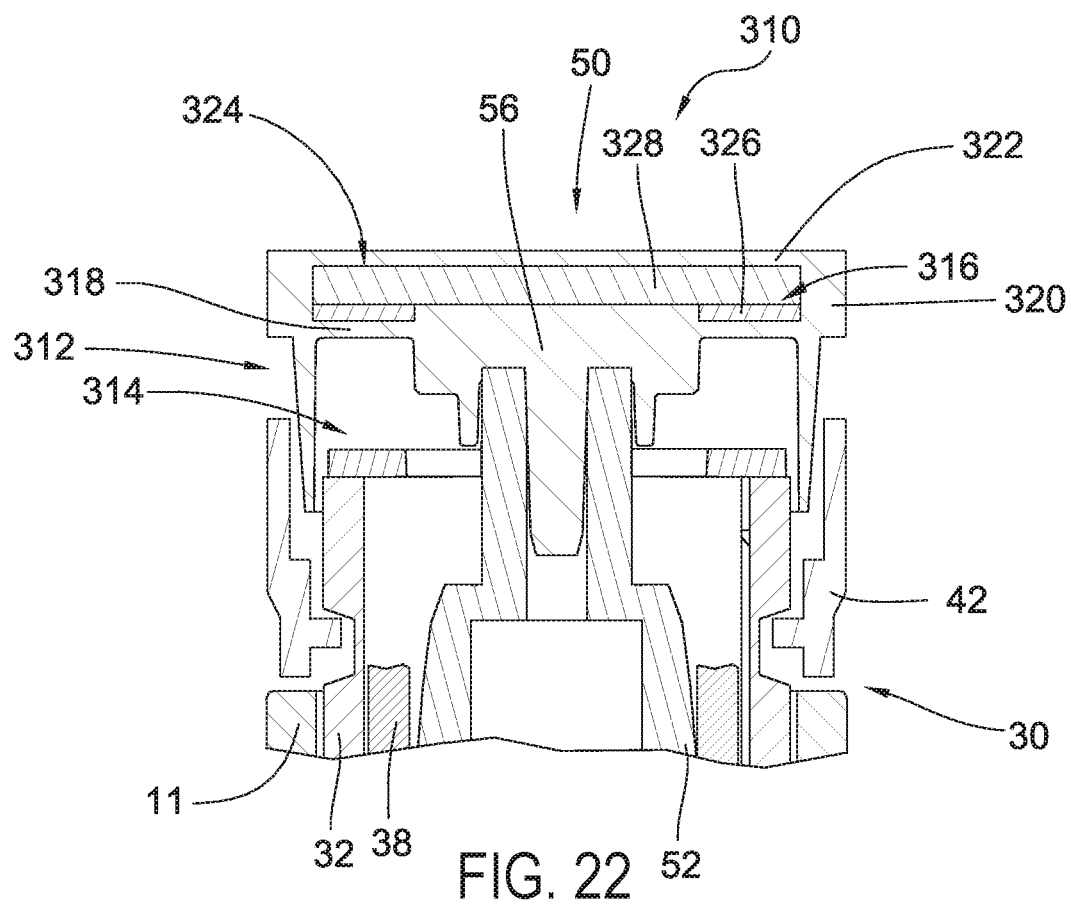
FIG. 22 is cross-sectional view of a dose detection system according to another embodiment, in which the sensor and sensed element are integrated into a medication delivery device.

The illustrative sensor system 230 is also useful as a system which is integrated into a medication delivery device, rather than being provided as a removable module. Referring to FIG. 22, there is shown a medication delivery device 310 substantially the same as device 10 in FIGS. 1-4. Medication delivery device 310 includes device body 11 and dose setting member 30 comprising dose dial member 32, flange 38, and skirt 42. These components are configured to function as previously described. Actuator 50 comprises clutch 52 and dose button 56 attached thereto. Dose button 56 is rotationally fixed with dose setting member 30 during dose setting. For dose delivery, this rotational fixing is disengaged, and dose setting member 30 rotates relative to dose button 56 in proportion to the amount of dose delivered.

Medication delivery device 310 differs from the device 10 of FIGS. 1-4 in the inclusion of a dose detection system 312, comprising sensed component 314 and sensor 316. Sensor 316 is integrated into dose button 56. Dose button 56 includes base wall 318, perimetric wall 320, and top wall 322, and together they form compartment 324. Sensor 316 comprises one or more sensor elements 326 supported within compartment 324. Similarly, one-piece dose button 56' shown in FIG. 27 may contain integrated sensor 316 and compartment 324.

An electronics assembly 328 is also received within compartment 324 and is operably connected with sensor elements 326. Electronics assembly 328 further includes a controller 330. Controller 328 is coupled with sensor elements 320 to receive the sensor output and to thereby determine information concerning the medication delivery device and/or its contents.

Sensed component 314 is attached to dose setting member 30. As for the embodiment of FIGS. 18-21, sensed component 314 comprises a metal band or other sensed element which has a unique angular profile. Sensed component 314 is shown attached to dose dial member 32, but it may as well be attached to other components of dose setting member 30. Sensor 316 is positioned and configured to detect the relative angular position of sensed component 314.

This embodiment differs from FIGS. 18-21 in that the components of dose detection system 312 are integrated into medication delivery device 310. In other respects, the sensing operation proceeds as previously described, with the dose detection system operating to detect the type of medication delivery device, the type of medication, and/or the amount of dose delivered by the medication delivery device, etc. In yet another alternative, sensed component 314 is integrated into medication delivery device 310, but sensor 316 is contained by a removable module as previously described.

Figure 23A:
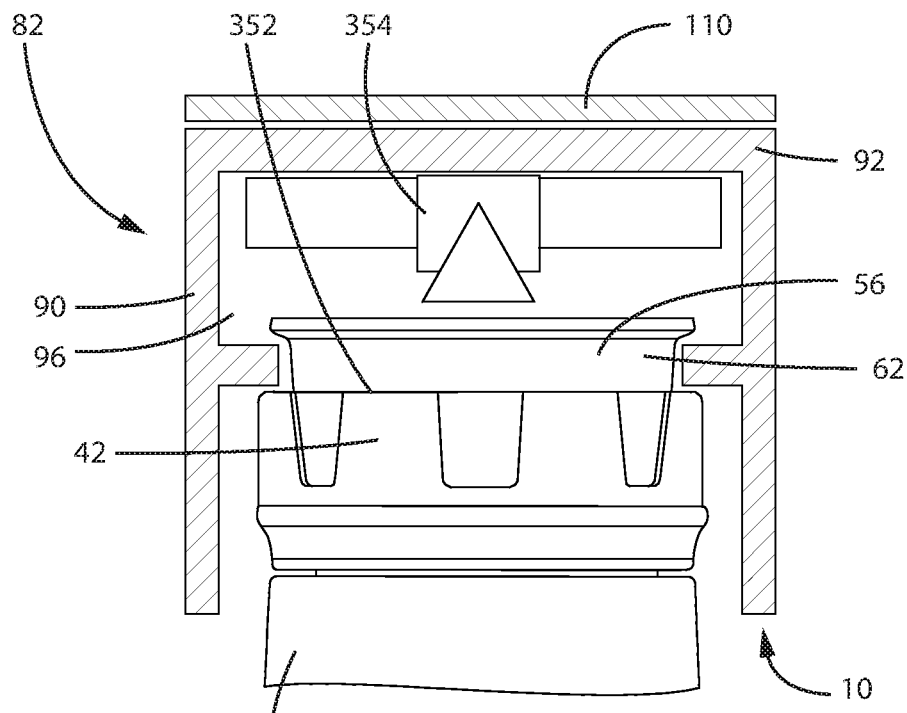
FIGS. 23A-C show in diagrammatic views an exemplary embodiment of a dose detection system utilizing optical sensing of the rotation and/or position of a skirt relative to a sensor component.
Figure 23B:
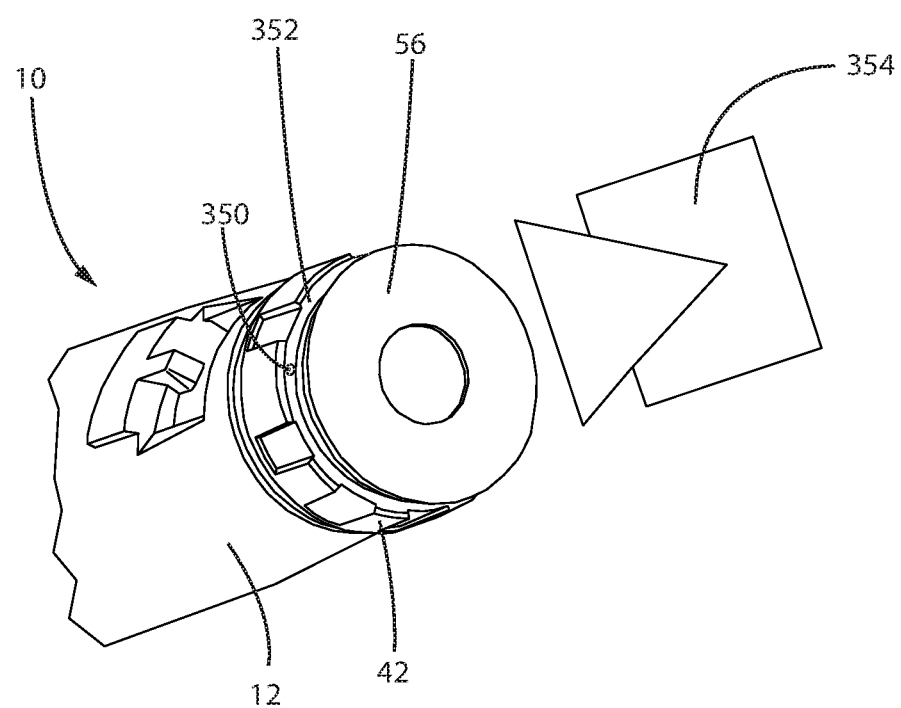
Figure 23C:
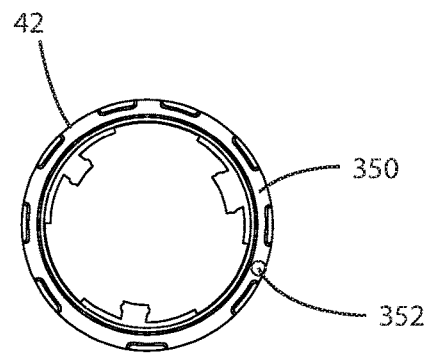

Referring to FIGS. 23A-C, there is shown an alternative embodiment employing optical sensing. As previously described, module 82 is attached to medication delivery device 10, which includes dose button 56 and skirt 42. The sensed element comprises one or more detectable marks 350 applied to the upper surface 352 of skirt 42. The marks may comprise, for example, spots of visible or invisible ink attached to skirt 42. The sensor system comprises a camera assembly 354 mounted within compartment 96. Camera assembly 354 is positioned and includes suitable optics to track the detectable mark(s) throughout rotation of skirt 42 relative to module 82.

Figure 24A:
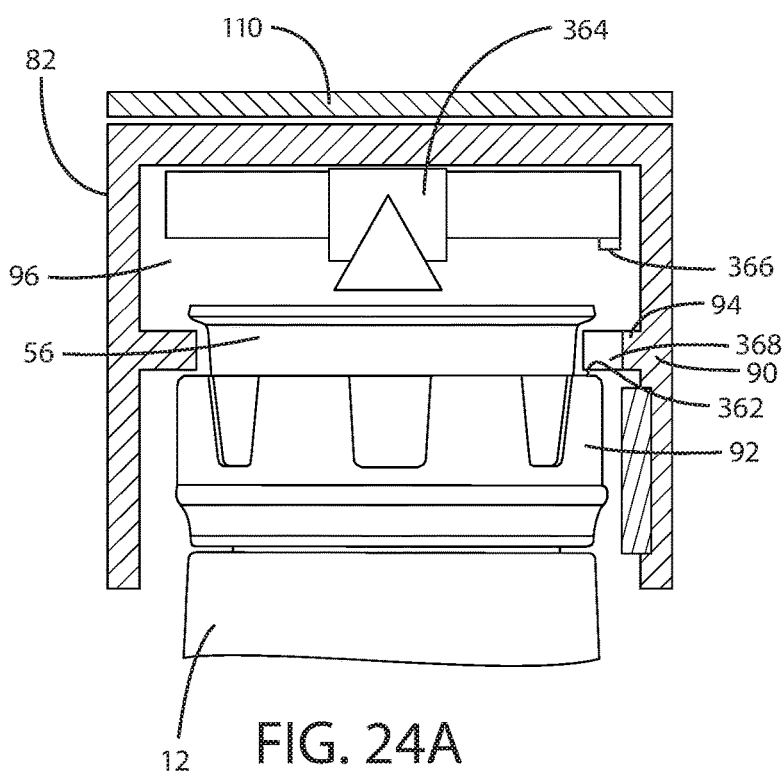
FIGS. 24A-B show in diagrammatic views another exemplary embodiment of a dose detection system utilizing optical sensing of the rotation and/or position of a flange relative to a sensor component.
Figure 24B:
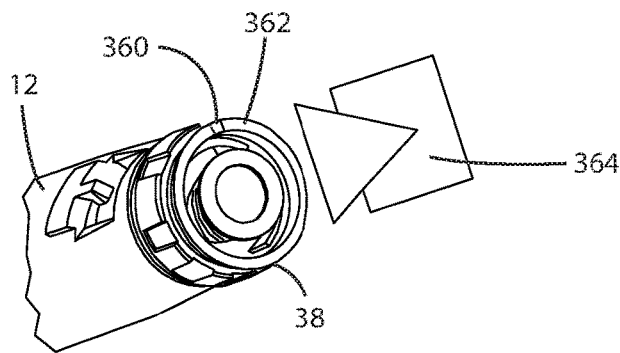

In a similar embodiment also using optical sensing, shown in FIGS. 24A-B, there again is provided a module 82 attached to medication delivery device 10. The sensed component comprises one or more detectable marks 360 applied to the upper surface 368 of flange 38. Camera assembly 364 is positioned and includes suitable optics to track the detectable mark(s) 360 throughout rotation of flange 38 relative to module 82. For example, camera assembly 364 may include a lens 366 positioned in alignment with a window (not shown) of dose button 56, and optionally a notch 370 formed in tab 94 of side wall 90. Detectable marks 360 may be provided in various patterns to facilitate monitoring of rotation of flange 38. It will be appreciated that either of the embodiments of FIGS. 23 and 24 could alternatively, or additionally, be used to detect an absolute relative position of the skirt or flange based on the inclusion of unique detectable marks around the perimeter of the skirt or flange.

Figure 25A:
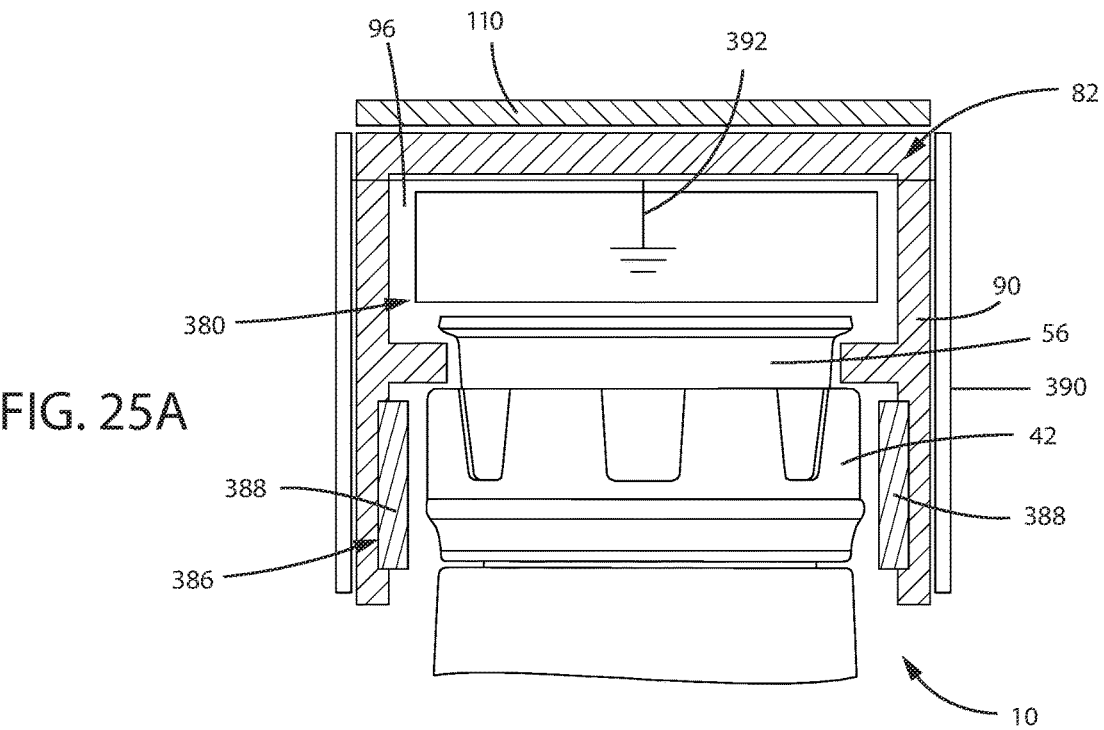
FIGS. 25A-C shows an exemplary embodiment of a dose detection system utilizing capacitive sensing.
Figure 25B:
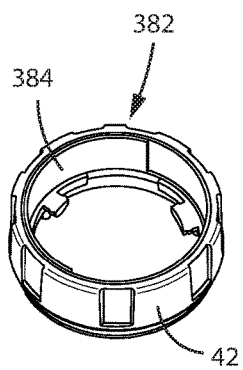
Figure 25C:
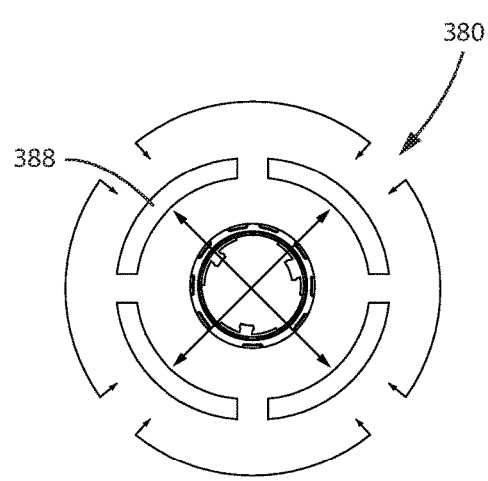
Figure 26:
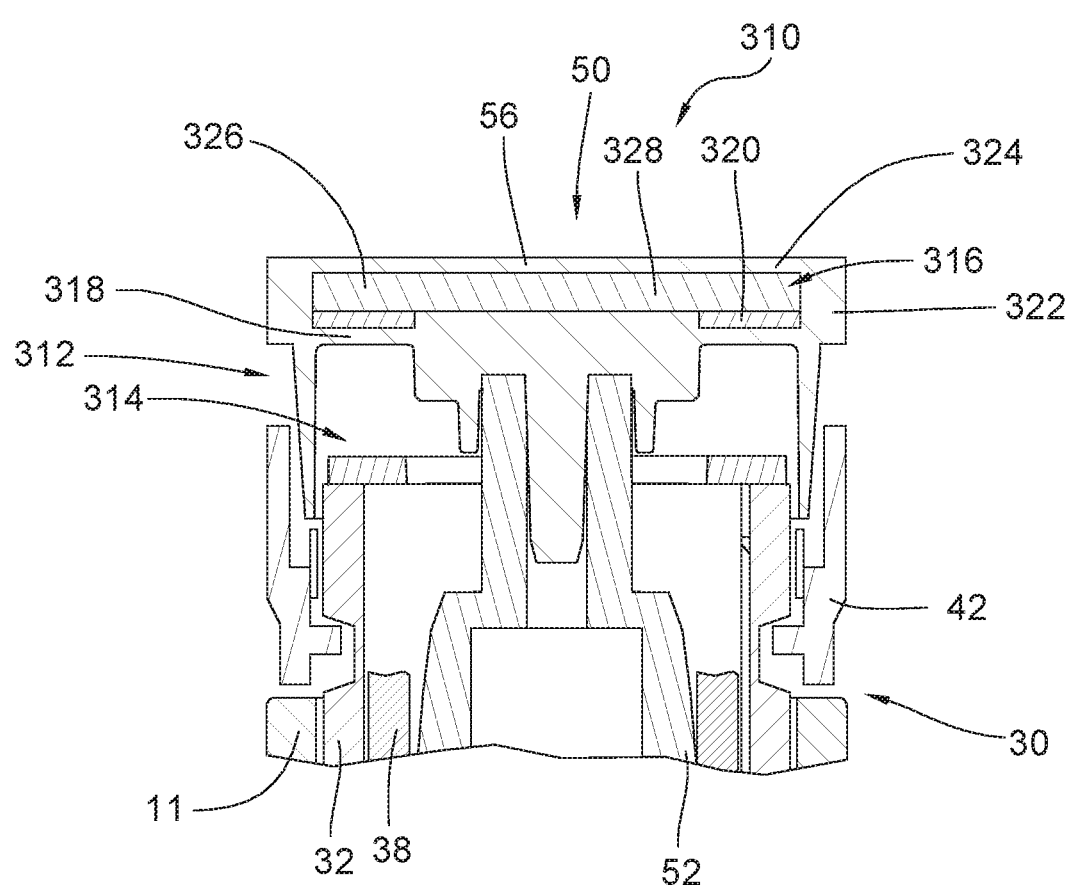
FIG. 26 is a cross-sectional view of a further exemplary medication delivery device of the present disclosure.

The sensor system is alternatively exemplified in FIGS. 25A-C as a capacitive sensor system 380. Sensor system 380 utilizes a sensed element 382 comprising a metal band 384 attached to skirt 42. Sensor system 380 further includes a sensor 386 comprising one or more sensing elements, e.g. antennas or armatures 388, mounted to side wall 90 opposite metal band 384. The metal band for example covers half of the circumference of skirt 42 and creates capacitive coupling between each pair of armatures while it rotates on the Z axis. The two armature pairs 180° apart form two sensors in quadrature and provide a ratio-metric measurement of the angular position of the skirt.

Metal band 384 is shaped such that rotational positions of skirt 42 relative to module 82 may be detected. Metal band 384 has a shape which generates a varying signal upon rotation of skirt 42 relative to antennas 384. The shape of metal band 384 and the positions of the armatures produce a sine wave response as skirt 42 rotates. A shield 390 on the outside of module wall 90 is connected to the device ground 392 and provides isolation of the sensor during operation.

For purposes of illustration, metal band 384 is shown as a single, cylindrical band extending halfway around the interior of skirt 42. However, alternate configurations and locations of metal band 384 are contemplated. For example, the metal band may comprise multiple discrete metal elements. The metal band in the alternative may be attached to any portion of a component rotationally fixed to skirt 42 during dose delivery, such as flange 38 or dial member 32. The metal band may comprise a metal element attached to the rotating member on the inside or the outside of the member, or it may be incorporated into such member, as by metallic particles incorporated in the component, or by over-molding the component with the metal band. In the embodiment illustrated in FIG. 27, dose button 56' of the illustrated device 10 is one piece which combines both skirt 42 and the dose button 56 of FIGS. 1-4. In this embodiment, with reference to FIGS. 11A and 11B, flange 38 is attached to dose dial member 32 and cooperates with clutch 52 to selectively couple dose dial member 32 with the one-piece dose button 56'. The radial exterior surface of one-piece dose button 56' provides a surface external of body 11 to use in rotating the dial member 32.

The dose detection systems have been described by way of example with particular designs of a medication delivery device, such as a pen injector. However, the illustrative dose detection systems may also be used with alternative medication delivery devices, and with other sensing configurations, operable in the manner described herein. Any of the devices described herein may comprise any one or more of medications described herein, such as, for example, within the cartridge of the device.

The invention claimed is:

1. A medication delivery device comprising:
  a device body;
  a dose setting member attached to said device body and rotatable relative to said device body during dose delivery;
  a ring-shaped sensed element rotationally fixed with said dose setting member;
  an actuator attached to said device body and movable relative to said device body during dose delivery;
  a dose delivery measurement module removably attached to the actuator, including a plurality of rotation sensors attached to said module, equi-radially spaced apart and axially over said ring-shaped sensed element and responsive to relative rotation of said ring-shaped sensed element relative to said actuator during dose delivery; and
  a controller responsive to said rotation sensors to detect an amount of rotation of said dose setting member relative to said actuator during dose delivery.

2. The medication delivery device of claim 1 in which said ring-shaped sensed element is directly attached to said dose setting member.

3. The medication delivery device of claim 1 in which said ring-shaped sensed element comprises a surface feature of said dose setting member.

4. The medication delivery device of claim 1 in which said dose setting member is rotationally fixed to said actuator during dose setting, said dose setting member and said actuator together are configured to rotate and move axially relative to said device body during dose setting, said dose setting member being rotatable relative to said actuator during dose delivery, said actuator is configured to move axially and said dose setting member is configured to rotate relative to said actuator during dose delivery.

5. The medication delivery device of claim 1 in which said module includes inward projections configured to attach said module to a dose button of said actuator.

6. The medication delivery device of claim 5 in which said module includes a lower cylindrical wall opposed to a portion of said dose setting member, said ring-shaped sensed element being rotationally fixed to the portion of said dose setting member, said rotation sensors being coupled to a circuit board that is rotationally fixed to said module.

7. The medication delivery device of claim 5 in which each of said rotation sensors is a magnetic, optical, inductive or capacitive sensor.

8. The medication delivery device of claim 7 in which each of said rotation sensors is adapted to produce outputs in response to changes in a magnetic field, wherein a portion of each of the rotation sensors is disposed extended beyond an outer circumference of the ring-shaped sensed element, said controller being responsive to the outputs from said rotation sensors to detect the amount of rotation of said dose setting member relative to said actuator during dose delivery.

9. The medication delivery device of claim 5 in which said actuator is movable axially relative to said dose setting member and has a first position relative to said dose setting member in which said actuator is rotationally fixed to said dose setting member, and has a second position relative to said dose setting member in which said actuator is free to rotate relative to said dose setting member.

10. The medication delivery device of claim 5 and further including a switch responsive to axially applied pressure to activate the rotation sensors.

11. The medication delivery device of claim 5 in which said dose setting member comprises at least one of a skirt, a flange, a dial member, and a surface feature.

12. The medication delivery device of claim 1, in which said device body includes a reservoir containing a medication.

13. A method of determining an amount of a delivered dose comprising:
  simultaneously rotating a dose setting device and an actuator coupled to a delivery measurement removable module relative to a body of a medication delivery device to set a dose on the medication delivery device, the dose setting device of the medication delivery device including a magnetic ring comprising one or more dipoles, and the delivery measurement removable module including a plurality of magnetic sensors, each having a portion disposed extended beyond an outer circumference of the magnetic ring;
  following the dose setting, moving the actuator distally relative to the body and thereby causing the dose setting member to rotate relative to the actuator and the delivery measurement removable module during the distal movement;
  during said moving, detecting a relative rotation of the magnetic ring using the magnetic sensors; and
  determining an amount of the delivered dose based on the detected relative rotation.

14. The method of claim 13 in which the dose setting device is rotationally fixed to the actuator during dose setting, and in which the dose setting device is free to rotate relative to the actuator during dose delivery.

15. The method of claim 14 in which, after setting the dose and prior to delivering the dose, the actuator is moved axially toward the dose setting device to release the dose setting device from being rotationally fixed to the actuator.

16. A dose delivery measurement module for use with a medication delivery device including a dose setting member and a ring-shaped, bipolar magnet attached thereto that rotates relative to an actuator during dose delivery, comprising:
  a module housing adapted to be removably attached to the actuator of a medication delivery device;
  a plurality of rotation magnetic sensors attached to said module housing, equi-radially spaced apart, and positioned to sense a rotation of a ring-shaped, bipolar magnet of a dose setting member relative to the actuator, wherein the rotation magnetic sensors are radially spaced such that a portion of each of the rotation magnetic sensors is disposed extended beyond an outer circumference of the ring-shaped, bipolar magnet; and
  a controller attached to said housing and responsive to the rotation magnetic sensors to detect an amount of rotation of the ring-shaped, bipolar magnet of the dose setting member relative to the actuator during a dose delivery, said module housing defining a compartment located to be proximal of the actuator when the module housing is attached to the actuator, said controller and said rotation magnetic sensors being received within the compartment.

17. The module of claim 16 in which the module housing includes a physical shape for frictionally engaging a surface of the actuator.

18. The module of claim 16 in which said module housing is rotationally fixed to said dose setting member during dose setting, said module housing and the dose setting member together rotating and moving axially relative to said device body during dose setting, said module housing and the dose setting member being rotatable relative to one another during dose delivery.

19. The module of claim 18 in which each of said magnetic sensors is adapted to produce outputs in response to changes in a magnetic field, said controller being responsive to the outputs from said magnetic sensors to detect the amount of rotation of said dose setting member relative to said module housing during dose delivery.

20. The module of claim 19 in which said module housing coupled to the actuator is together movable axially relative to said dose setting member and has a first position relative to said dose setting member in which said module housing is rotationally fixed relative to said dose setting member, and has a second position relative to said dose setting member in which said actuator together with the module housing is free to rotate relative to said dose setting member.

* * * * *